US012773212B2

(12) United States Patent
Tenne et al.

(10) Patent No.: US 12,773,212 B2
(45) Date of Patent: Oct. 27, 2026

(54) DEVICES, SYSTEMS, AND METHODS FOR OCCLUDING AND ALLOWING FLUID ACCESS TO OCCLUSED AREA

(71) Applicant: GYRUS ACMI, INC., Westborough, MA (US)

(72) Inventors: Dirk Tenne, Seattle, WA (US); Jay Parker, Coopersburg, PA (US)

(73) Assignee: Gyrus ACMI, Inc., Westborough, MA (US)

( * ) Notice: Subject to any disclaimer, the term of this patent is extended or adjusted under 35 U.S.C. 154(b) by 872 days.

(21) Appl. No.: 17/934,435

(22) Filed: Sep. 22, 2022

(65) Prior Publication Data

US 2023/0100660 A1 Mar. 30, 2023

Related U.S. Application Data

(60) Provisional application No. 63/247,891, filed on Sep. 24, 2021.

(51) Int. Cl.
*A61B 17/12* (2006.01)
*A61M 16/04* (2006.01)
*A61M 25/00* (2006.01)

(52) U.S. Cl.
CPC .. *A61B 17/12104* (2013.01); *A61B 17/12136* (2013.01); *A61M 16/0404* (2014.02);
(Continued)

(58) Field of Classification Search
CPC .............. A61M 16/04; A61M 16/0404; A61M 16/0406; A61M 16/0434; A61M 16/0463;
(Continued)

(56) References Cited

U.S. PATENT DOCUMENTS 3,087,493 A * 4/1963 Schossow ......... A61M 16/0488 128/207.15
3,528,427 A * 9/1970 Sheridan ............... A61M 27/00 604/45

(Continued)

FOREIGN PATENT DOCUMENTS

WO 2023049799 3/2023

OTHER PUBLICATIONS

"International Application Serial No. PCT US2022 076858, International Search Report mailed Jan. 4, 2023", 4 pgs.

(Continued)

*Primary Examiner* — Douglas Y Sul
(74) *Attorney, Agent, or Firm* — Schwegman Lundberg & Woessner, P.A.

(57) ABSTRACT

Disclosed embodiments include apparatuses, systems, and methods for assessing collateral ventilation. An illustrative embodiment includes a flexible insertion catheter device includes an outer tube having an inner diameter. The outer tube includes a plurality of ports at a distal end and an occlusion device filling port located proximal from the plurality of ports. Also, the flexible insertion catheter device includes an inner tube receivable within the outer tube. The inner tube includes a flow lumen and an outer diameter less than the inner diameter of the outer tube. The flexible insertion catheter device further includes an occlusion device attachable to the outer tube and configured to selectively seal a bronchial passageway to occlude a lobe of a lung.

19 Claims, 24 Drawing Sheets

(52) U.S. Cl.
CPC .... *A61M 16/0434* (2013.01); *A61M 16/0484* (2014.02); *A61M 25/007* (2013.01); *A61M 2025/0004* (2013.01)

(58) Field of Classification Search
CPC .......... A61M 16/0475; A61M 16/0484; A61M 16/0486; A61M 25/007; A61M 2025/0004; A61M 2025/1052; A61B 17/12136; A61B 17/12104; A61B 17/1204; A61B 5/6853
See application file for complete search history.

(56) References Cited

U.S. PATENT DOCUMENTS

| | | | | | |
|---|---|---|---|---|---|
| 3,593,713 | A * | 7/1971 | Bogoff | A61M 25/0017 | 604/27 |
| 3,734,100 | A * | 5/1973 | Walker | A61M 16/0484 | 128/207.15 |
| 3,971,385 | A * | 7/1976 | Corbett | A61M 16/0445 | 128/207.15 |
| 4,182,343 | A * | 1/1980 | Inaba | A61M 27/00 | 604/268 |
| 4,637,389 | A * | 1/1987 | Heyden | A61M 16/0479 | 604/35 |
| 5,728,063 | A * | 3/1998 | Preissman | A61M 25/0054 | 604/103.09 |
| 6,179,856 | B1 * | 1/2001 | Barbere | A61M 25/1006 | 604/97.02 |
| 2003/0051733 | A1 * | 3/2003 | Kotmel | A61B 5/087 | 128/207.14 |
| 2008/0097384 | A1 | 4/2008 | Pacey | | |
| 2008/0228130 | A1 * | 9/2008 | Aljuri | A61M 16/0486 | 604/24 |
| 2012/0080037 | A1 * | 4/2012 | Guyuron | A61M 16/0431 | 128/207.18 |
| 2019/0381288 | A1 * | 12/2019 | Mock | A61M 25/1002 | |
| 2020/0093991 | A1 | 3/2020 | Schwartz et al. | | |
| 2020/0359966 | A1 | 11/2020 | Taylor | | |
| 2024/0017029 | A1 * | 1/2024 | D'Errico | A61M 16/0488 | |

OTHER PUBLICATIONS

"International Application Serial No. PCT US2022 076858, Written Opinion mailed Jan. 4, 2023", 5 pgs.
"International Application Serial No. PCT/US2022/076858, International Preliminary Report on Patentability mailed Apr. 4, 2024", 7 pgs.

* cited by examiner

DEVICES, SYSTEMS, AND METHODS FOR OCCLUDING AND ALLOWING FLUID ACCESS TO OCCLUSED AREA

PRIORITY CLAIM

This application claims the benefit of priority to U.S. Patent Application Ser. No. 63/247,891, filed Sep. 24, 2021, the contents of which are hereby incorporated by reference in their entirety.

BACKGROUND

The statements in this section merely provide background information related to the present disclosure and may not constitute prior art.

Current occlusion devices used in a lung diagnostic or treatment scenarios include an occluding member (e.g., a balloon) and a pneumatic or fluidic device for accessing a distal side of the occluding member when disposed within the lung. The pneumatic or fluidic device includes a single distal port. Mucus or other material or fluid in the lung may become lodged in the single distal port, thus reducing the operational capabilities of the pneumatic or fluid interaction with the lung. The single distal port may also come into contact with an airway wall, thereby preventing air or fluid flow into or out of the lung.

SUMMARY

Disclosed embodiments include devices, systems, and methods for occluding and applying controlled fluid flow into or out of an occluded area.

In an illustrative embodiment, a flexible insertion catheter device includes an outer tube having an inner diameter. The outer tube includes a plurality of ports at a distal end and an occlusion device filling port located proximal from the plurality of ports. Also, the flexible insertion catheter device includes an inner tube receivable within the outer tube. The inner tube includes a flow lumen and an outer diameter less than the inner diameter of the outer tube. The flexible insertion catheter device further includes an occlusion device attachable to the outer tube and configured to selectively seal a bronchial passageway to occlude a lobe of a lung.

In other embodiments, a seal is located between the flow lumen and an inflation lumen located between the outer tube and the inner tube. The inflation lumen receives from an inflation device a flow of gas to selectively inflate and expand the occlusion device to sealably occlude the bronchial passageway.

In still other embodiments, the inner tube extends distal from the seal and includes a plurality of ports distal of the seal. Thus, the ports of the outer tube and the inner tube mitigate migration of blocking mucus and provide other fluid options in the event a couple of the ports get blocked.

In yet other embodiments, the ports of the inner tube have larger diameters than the ports of the outer tube. The smaller ports of the outer tube resist intake of mucus or tissue.

In still yet other embodiments, the ports of the inner tube are offset at least one of radially or longitudinally from the ports of the outer tube. The offset ports reduce ability of mucus or tissue to be ingested into to the outer and inner tubes.

Further features, advantages, and areas of applicability will become apparent from the description provided herein. It will be appreciated that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, with emphasis instead being placed upon illustrating the principles of the disclosed embodiments. In the drawings.

DETAILED DESCRIPTION

The following description is merely illustrative in nature and is not intended to limit the present disclosure, application, or uses. It will be noted that the first digit of three-digit reference numbers and the first two digits of four-digit reference numbers correspond to the first digit of one-digit figure numbers and the first two-digits of the figure numbers, respectively, in which the element first appears.

The following description explains, by way of illustration only and not of limitation, various embodiments of systems, apparatuses, and methods for assessing collateral ventilation between lobes of a lung. The focus of the disclosure is an occlusion catheter discussed below in reference to FIGS. 2A-5. The other discussion herein outlines supporting systems and related capabilities. For example, the system discussed in FIGS. 1A and 1B can utilize the occlusion catheter for assessing collateral ventilation between lobes of a lung.

Figure 1B:
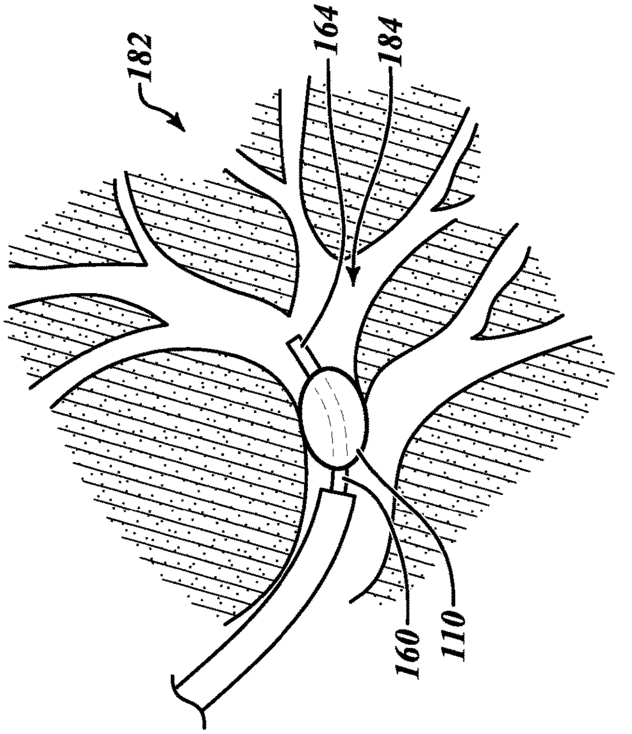
FIG. 1B is an enlarged view of a region B in FIG. 1A showing an occlusion device positioned in a bronchial passageway.
Figure 1A:
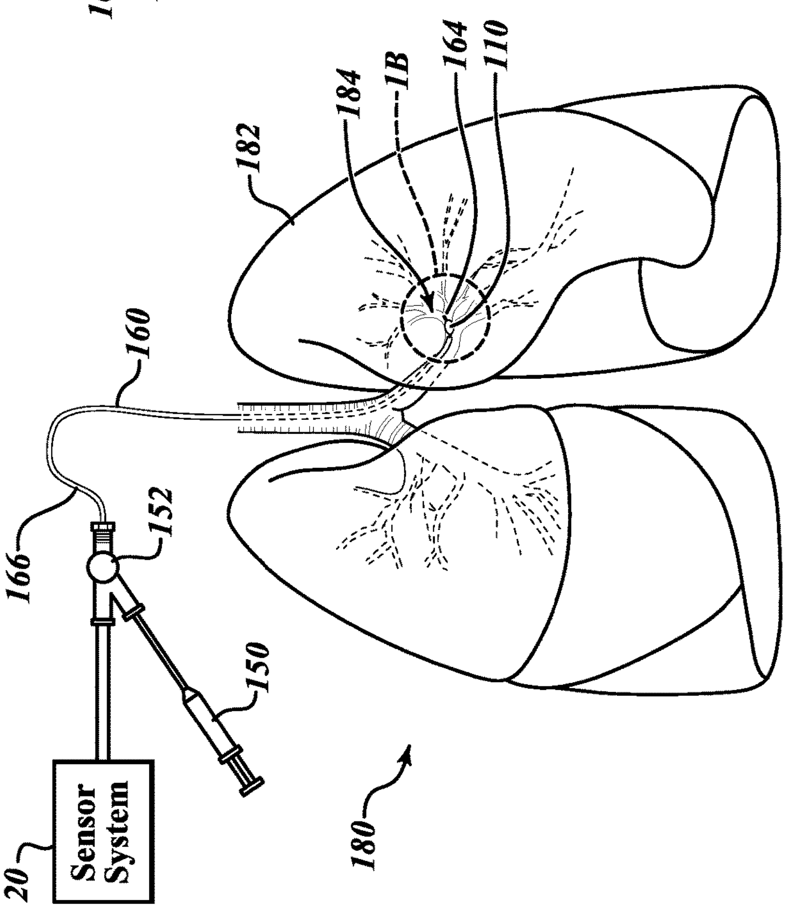
FIG. 1A is a schematic diagram of an illustrative system for assessing lung activity.

Referring to FIG. 1A and 1B and given by way of non-limiting overview, in various embodiments an illustrative system 100 can assess lung lobe operations by testing a lobe 182 of a lung 180. The system 100 includes an occlusion device 110 insertable into a bronchial passageway 184 to the lobe 182 of the lung 180 to be tested. The occlusion device 110 includes an insertion tube 166 having a flow lumen 160 that sealably extends from a dual-lumen handle device 152 through the occlusion device 110 to a distal end 164 to occlude a target location of the lung 180. The system 100 is configured to convey (positive pressure) or receive (passive) airflow to/from the lobe 182 via the occlusion device 110. A sensor system 20 is couplable to one of the lumens of the dual-lumen handle device 152 that is connected to the flow lumen 160. The sensor system 20 includes components configured to determine pressure values and from the determined pressure values make an assessment of the occluded lung lobe.

The occlusion device 110 is inflated to block the passageway 184 to the lobe 182. In various embodiments, the occlusion device 110 is an inflatable device that is selectively inflated or deflated via an inflation lumen (not shown in FIG. 1A) that coextends with the flow lumen 160. The configuration of the occlusion device is described in further detail with regard to FIGS. 2A-4E. The flow lumen 160 extends to and through the occlusion device 110 to the distal end 164 that extends into the lobe 182.

Briefly referring back to FIG. 1A, actuating the inflation device 150 may drive the inflation gas through a second lumen of the dual-lumen handle device 152 into an inflation lumen of the insertion tube 166, then into the occlusion device 110 to inflate it. Thus, when the inflation device 150 is a syringe, a user may depress a plunger on the syringe to drive the inflation gas through the inflation lumen to inflate the occlusion device 110.

Figure 2A:
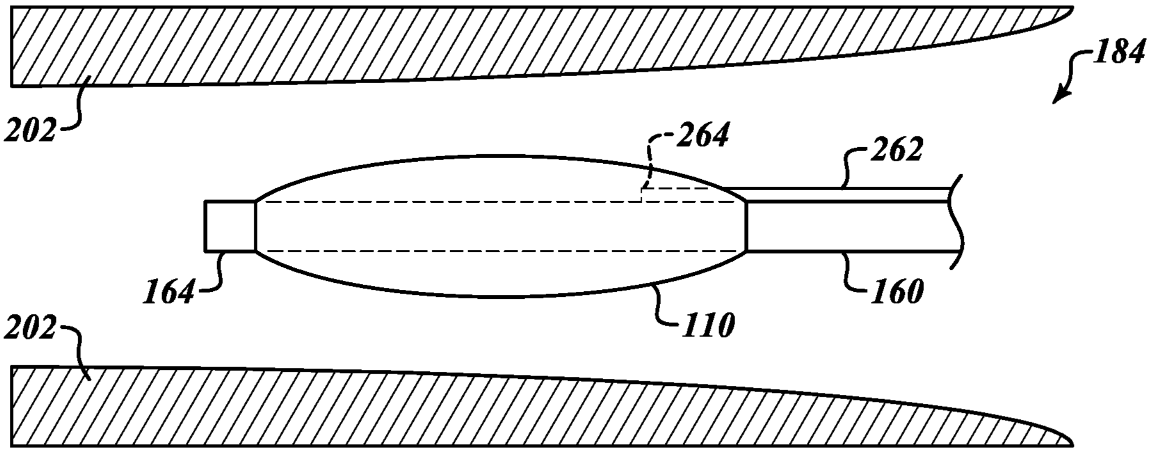
FIGS. 2A and 2B are partial cross-sectional views of an occlusion device of the system of FIGS. 1A and 1B.
Figure 2B:
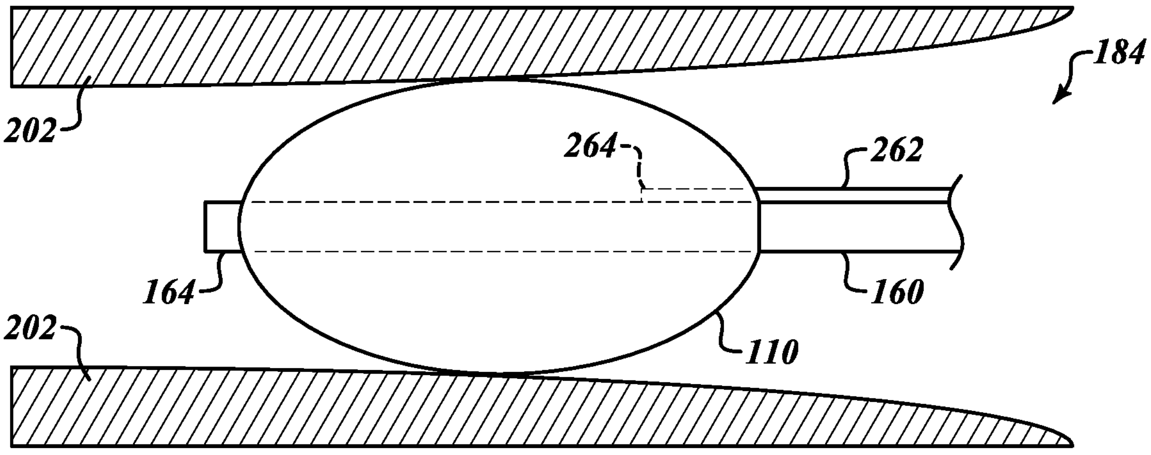

In various embodiments, the system 100 occludes the lobe 182 of the lung 180 to be tested by blocking the bronchial passageway 184 to the lobe 182 with the occlusion device 110. Referring to FIGS. 2A and 2B, the bronchial passageway 184 may be blocked by inserting the occlusion device 110 into the bronchial passageway 184 in between walls 202 of the bronchial passageway 184. As shown in FIG. 2A, the occlusion device 110 is in a deflated condition. The flow lumen 160 sealably extends through the occlusion device 110 with the distal end 164 of the flow lumen 160 extending into the bronchial passageway 184 beyond the occlusion device 110. The distal end 164 of the flow lumen 160 and the occlusion device 110 may be a balloon catheter. The flow lumen 160 coextends with and may be integrally formed with an inflation lumen 262. The inflation lumen 262 has a distal end 264 that extends into the interior of the occlusion device 110 such that an inflation gas passed through the inflation lumen 262 may inflate the occlusion device. In this example, the flow lumen 160 and the inflation lumen 262 can be formed as a single dual lumen catheter. In an example, the dual lumen catheter (160, 262) can be an extruded, or similarly formed, elongate member with the flow lumen 160 extending a distance further than the inflation lumen 262 on a distal end. In this example, the occlusion device 110 is formed around the flow lumen 160 that extends distally (forming distal end 164).

Referring now to FIG. 2B, the occlusion device 110 is in an inflated condition, thereby blocking the bronchial passageway 184 and occluding the lobe 182. The occlusion device 110 presses against the opposing walls 202 of the bronchial passageway 184, thereby blocking the flow of air into the bronchial passageway 184 except for a flow of gas introduced via the flow lumen 160.

Figure 3A:
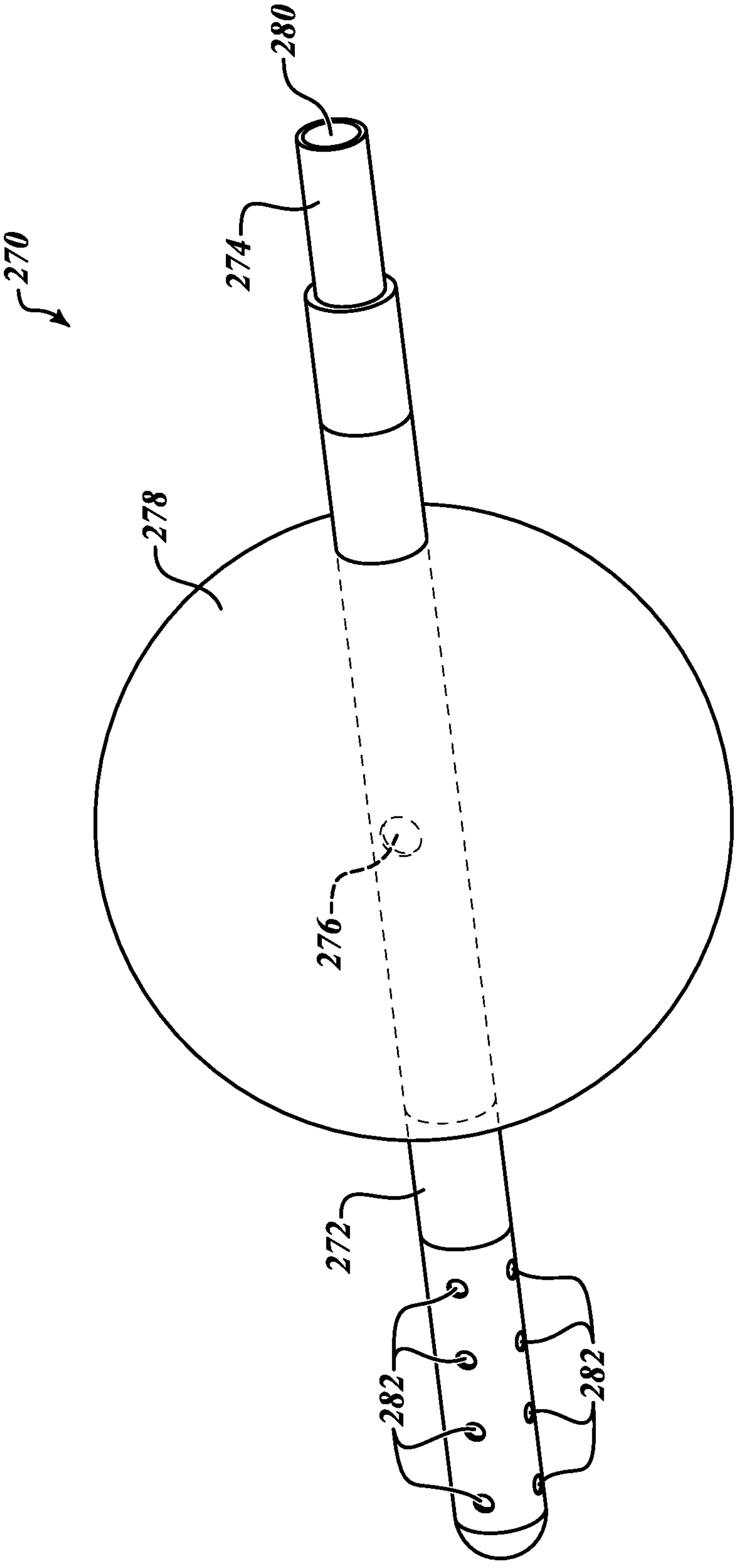
FIG. 3A is a perspective view of a distal end of an insertion portion of the system of FIG. 1A.
Figure 3B:
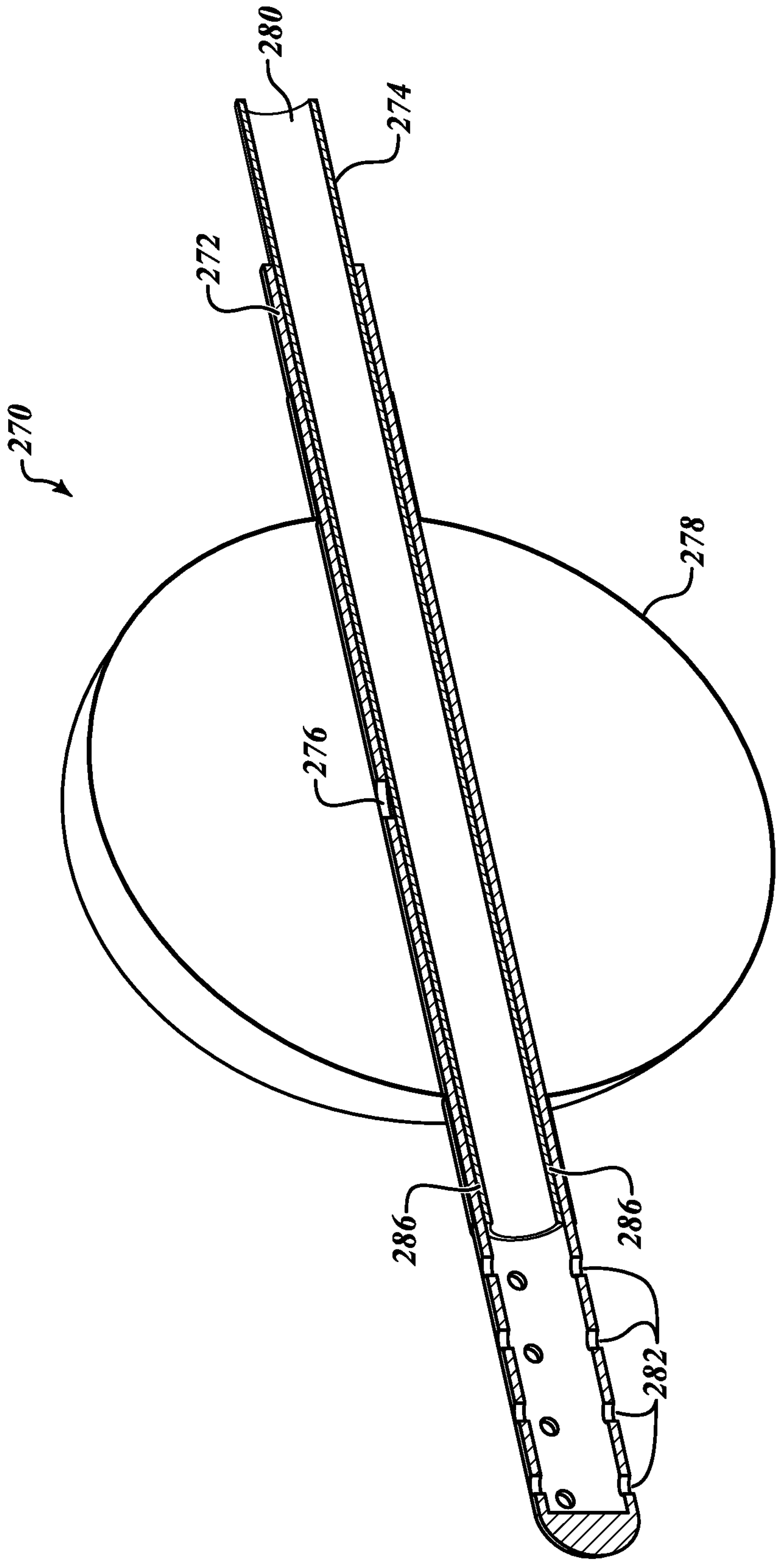
FIG. 3B is a perspective cross-sectional view of the distal end of an insertion portion of FIG. 3A.
Figure 3C:
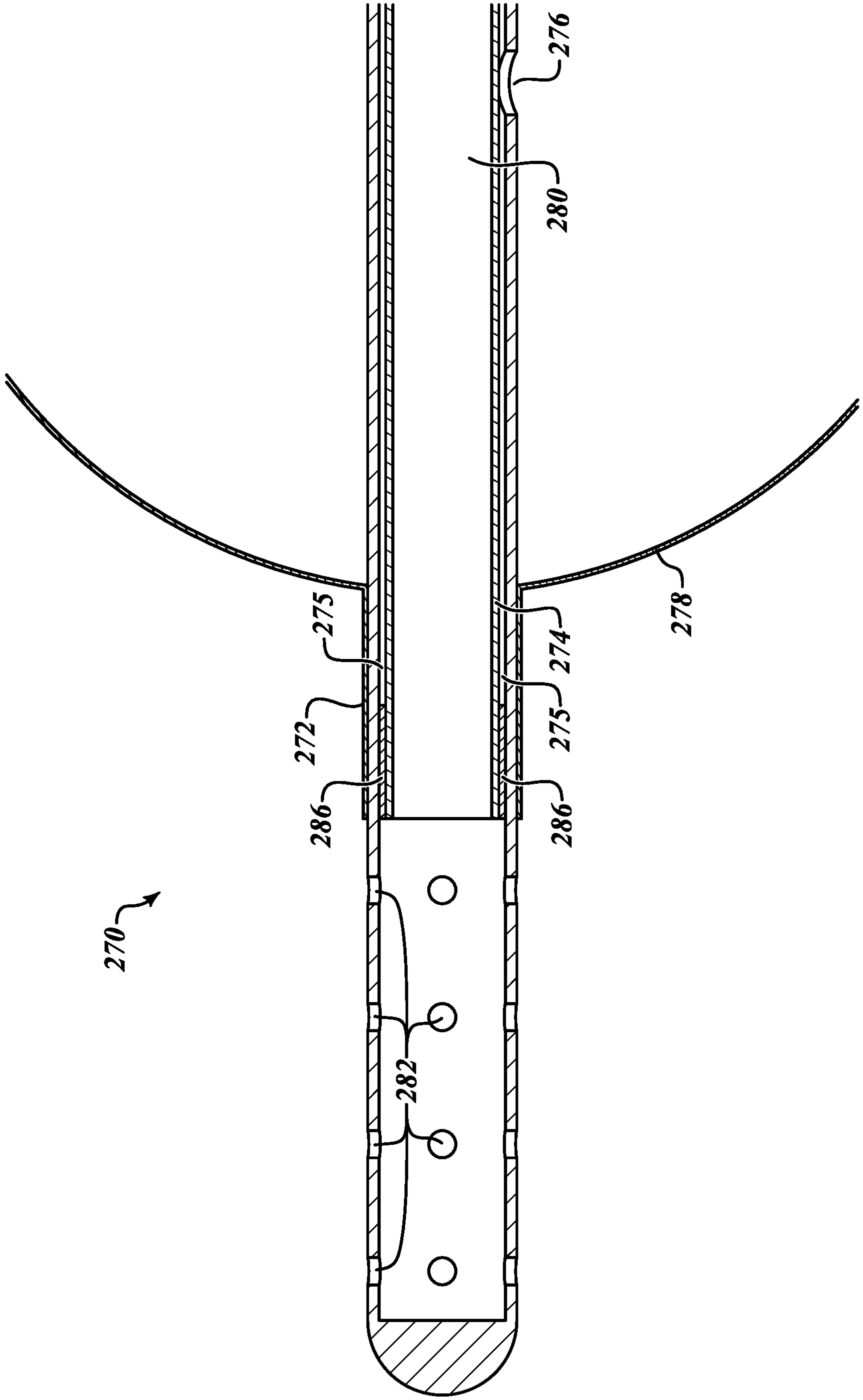
FIG. 3C is a side cross-sectional view of the distal end of an insertion portion of the system of FIG. 3A.

In various embodiments, as shown in FIGS. 3A-C, the bronchial passageway 184 may be blocked by an occlusion device 270. The occlusion device 270 functions like the occlusion device 110 of FIGS. 2A-B. However, the occlusion device 270 may be used in other locations within a patient where occlusion and controlled airflow may have benefits. The occlusion device 270 includes an outer catheter (or tube) 272, an inner catheter (or tube) 274 received within the outer catheter 272, and an inflatable balloon 278 received over the outer catheter 272. Note, while occlusion device 270 is discussed herein as having coaxial inner and outer catheters, the occlusion device 270 could also be formed as a dual (side-by-side) catheter similar to occlusion device 110 (except where the inner and outer catheter configuration provides unique characteristics not easily replicated in a dual lumen configuration). The outer catheter 272 includes a porous distal tip having side holes 282 for allowing air to pass to/from a flow lumen 280 that is comparable to the flow lumen 160 described above. A passage 275 formed between the outer catheter 272 and inner catheter 274 allows inflation air to flow around the inner catheter 274 to reach the balloon 274. The outer catheter 272 includes a side hole 276, collocated with the balloon 278. The side hole 276 provides air/fluid access between a sealed inner portion of the balloon 278 and a passageway (e.g., passage 275) located between the inner catheter 274 and the outer catheter 272. In an example, an annular seal 286 blocks the passageway (passage 275) between the inner catheter 274 and the outer catheter 272 from the distal porous tip with the side holes 282. The outer catheter 272, the inner catheter 274, and/or the annular seal 286 may be formed of a fusible material, such as, without limitations, Pebax®, metal, or other medical grade material. Thus, when heat is applied, the outer catheter 272, the inner catheter 274, and the annular seal 286 fuse together. A distal end of the inner catheter 274 is located at or near a distal end of the annular seal 286 and proximal of the side holes 282.

In various embodiments, the very distal end of the outer catheter 272 has a non-destructive shape, such as, without limitation, a rounded shape, square shape, tapered shape, or other non-destructive shape.

In various embodiments, the outer catheter 272 and the inner catheter 274 may be integrally formed using a dual lumen extrusion process. Also, the catheters 272 and 274 may be cylindrical, square, rectangular, or other shapes. The inner catheter 272 and the outer catheter 274 may be formed by attaching two tubes together with a medical grade adhesive or a shrink wrap material.

Figure 4A:
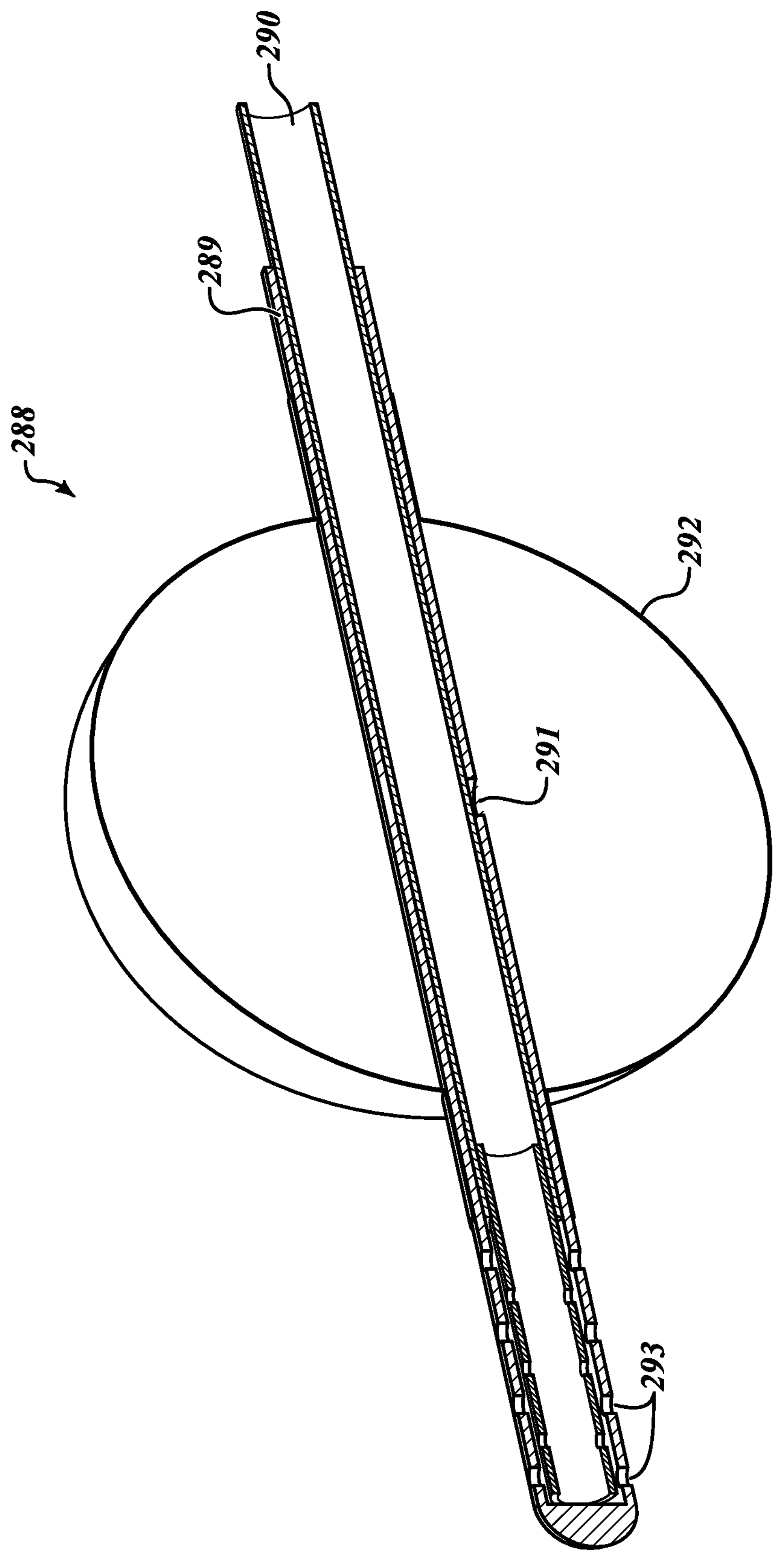
FIG. 4A is a perspective cross-sectional view of the distal end of an insertion portion of the system of FIG. 1A.
Figure 4B:
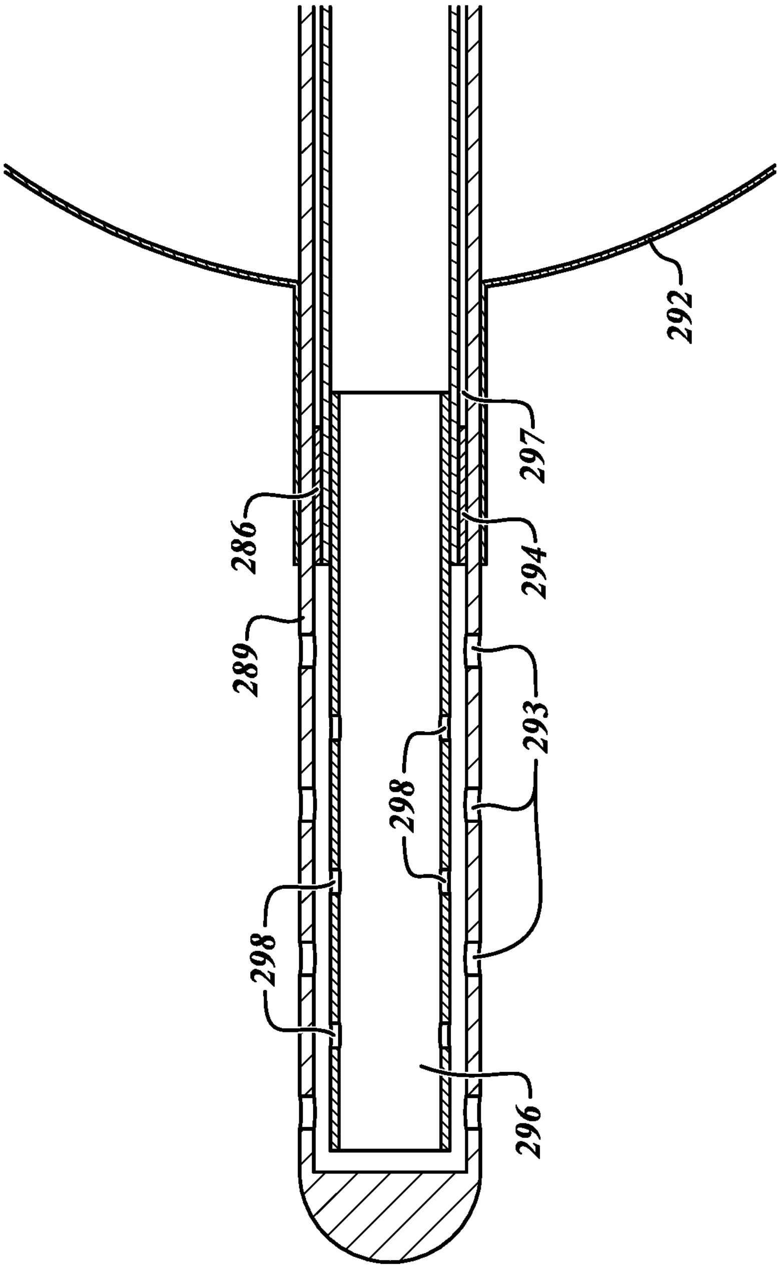
FIG. 4B is a zoomed-in cross-sectional view of the distal end of an insertion portion of the component of FIG. 4A.

In various embodiments, as shown in FIGS. 4A-B, the bronchial passageway 184 may be blocked by an occlusion device 288 that includes an outer catheter (or tube) 289 configured to receive an inner catheter (or tube) 290. The occlusion device 288 functions like the occlusion device 110 of FIGS. 2A-B. However, the occlusion device 288 may be used in other locations within a patient where occlusion and controlled airflow may have benefits. The outer catheter 289 includes a side hole 291 located between a distal end and a proximal end of an inflatable balloon 292. The distal end and proximal end of the inflatable balloon 192 are attached to the outer catheter 289. The side hole 291 provides access to a gap/passageway 297 located between the outer catheter 289 and the inner catheter 290. The passageway 297 extends to the handle and a port configured to receive a balloon inflation device.

The outer catheter 289 includes a distal porous section having side holes 293. The side holes 293 are located distal of where the distal end of the balloon 292 attaches to the outer catheter 289. A distal inner tube 296 is received within a distal end of the inner catheter 290. The distal inner tube 296 has an outer diameter that is approximately equal to an inner diameter of the inner catheter 290. The distal inner tube 296 includes side holes 298 configured to allow airflow between the airway, the side holes 293 of the outer catheter 289, and a lumen of the inner catheter 290. The side holes 298 may be offset longitudinally from the side holes 293. The distal end of the distal tube 296 may be open allowing for additional airflow between the lumen of the inner catheter 290 and the side holes 293 of the outer catheter 289. The lumen of the inner catheter 290 function similar to the flow lumen 160 described above. A sealing ring 294 is disposed at a distal end of the passageway 297 between the outer catheter 289 and the inner catheter 290. The sealing ring 294 provides a bond between the outer catheter 289 in the inner catheter 290, thus pneumatically separating the lumen of the inner catheter 290 and the passageway 297. The outer catheter 289, the inner catheter 290, the distal inner tube 296, and/or the sealing ring 294 may be formed of a fusible material, such as, without limitations, Pebax®, metal, or other medical grade material. Thus, when heat is applied, the outer catheter 289, the inner catheter 290, the distal inner tube 296, and the sealing ring 294 fuse together. Other attachment methods may be used, such as medical grade epoxies, shrink wrap, etc.

In various embodiments, the side holes 293 and 298 may be formed as slots, spiral cuts, or other geometric configuration providing access thru the respective tube. The side holes 293 and 298 may be machined, laser etched, chemically etched into the respective catheter.

Figure 4C:
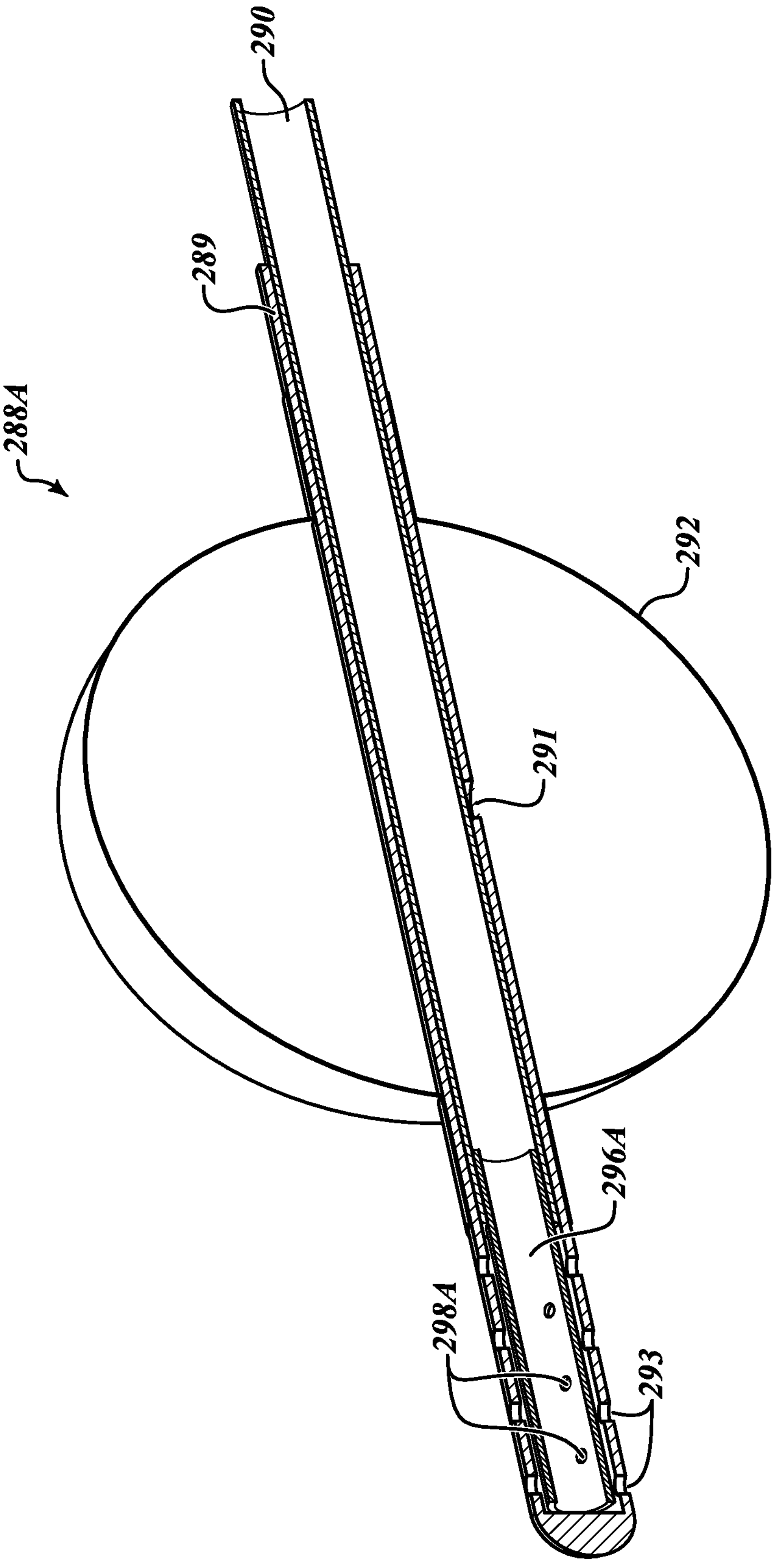
FIG. 4C is a perspective cross-sectional view of the distal end of an insertion portion of the system of FIG. 1A.
Figure 4D:
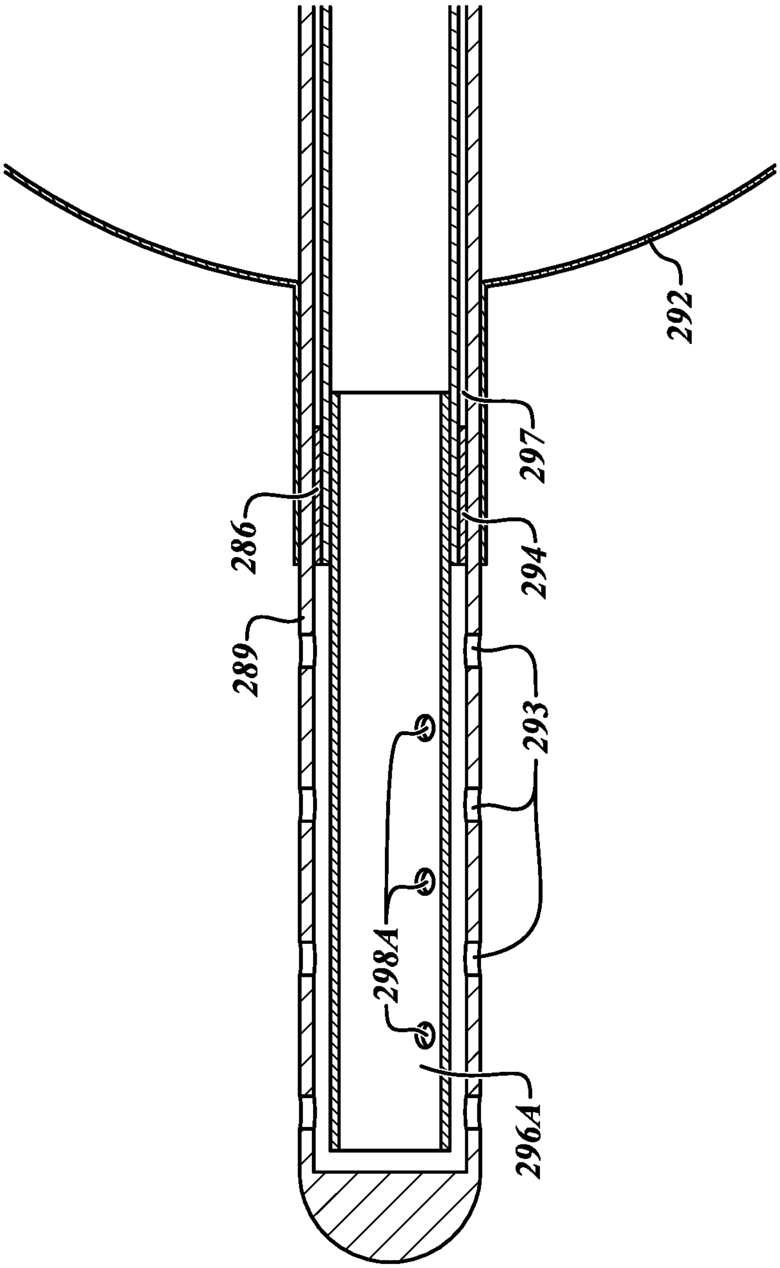
FIG. 4D is a zoomed-in cross-sectional view of the distal end of an insertion portion of the component of FIG. 4C.

In various embodiments, as shown in FIGS. 4C-D, the bronchial passageway 184 may be blocked by an occlusion device 288A that includes the outer catheter 289 and the inner catheter 290, such as described above. The occlusion device 288A functions like the occlusion device 110 of FIGS. 2A-B and may have applicability in other locations.

A distal inner tube 296A is received within a distal end of the inner catheter 290. The distal inner tube 296A has an outer diameter that is approximately equal to an inner diameter of the inner catheter 290. The distal inner tube 296A includes side holes 298A configured to allow airflow between the bronchial passageway 184, the side holes 293 of the outer catheter 289, and the lumen of the inner catheter 290. The side holes 298A are offset longitudinally and radially from the side holes 293. The distal end of the distal tube 296A may be open for allowing for additional airflow between the lumen of the inner catheter 290 and the side holes 293 of the outer catheter 289.

The outer catheter 289, the inner catheter 290, the distal inner tube 296A, and/or the sealing ring 294 may be formed of a fusible material, such as, without limitations, Pebax®, metal, or other medical grade material. Thus, when heat is applied, the outer catheter 289, the inner catheter 290, the distal inner tube 296A, and the sealing ring 294 fuse together.

Figure 4E:
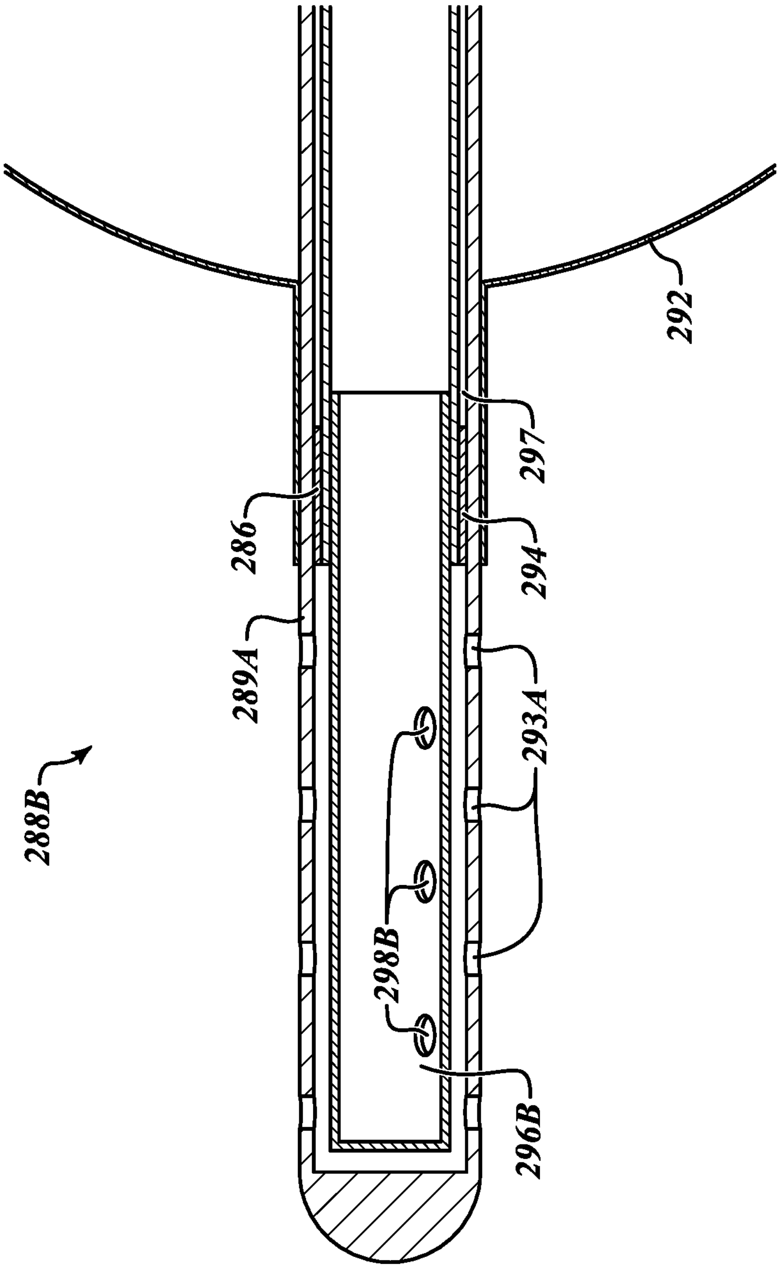
FIG. 4E is a zoomed-in cross-sectional view of the distal end of an insertion portion of the system of FIG. 1A.

In various embodiments, as shown in FIG. 4E, the bronchial passageway 184 may be blocked by an occlusion device 288B that includes an outer catheter 289A and the inner catheter 290, such as described above. The occlusion device 288B functions like the occlusion device 110 of FIGS. 2A-B and may have applicability in other locations. The outer catheter 289A include side holes 293A.

A distal inner tube 296B is received within a distal end of the inner catheter 290. The distal inner tube 296B has an outer diameter that is approximately equal to an inner diameter of the inner catheter 290. The distal inner tube 296B includes side holes 298B configured to allow airflow between the bronchial passageway 184, the side holes 293A of the outer catheter 289, and the lumen of the inner catheter 290. The side holes 298B may be offset longitudinally and/or radially from the side holes 293A. The side holes 298B may have any position relative to the side holes 293A. The side holes 298B may be larger than the side holes 293A for minimizing amount of tissue or fluid that could get sucked into the outer catheter 289A. The distal end of the distal tube 296B may be open allowing airflow between the lumen of the inner catheter 290 and the side holes 293A.

Figure 5:
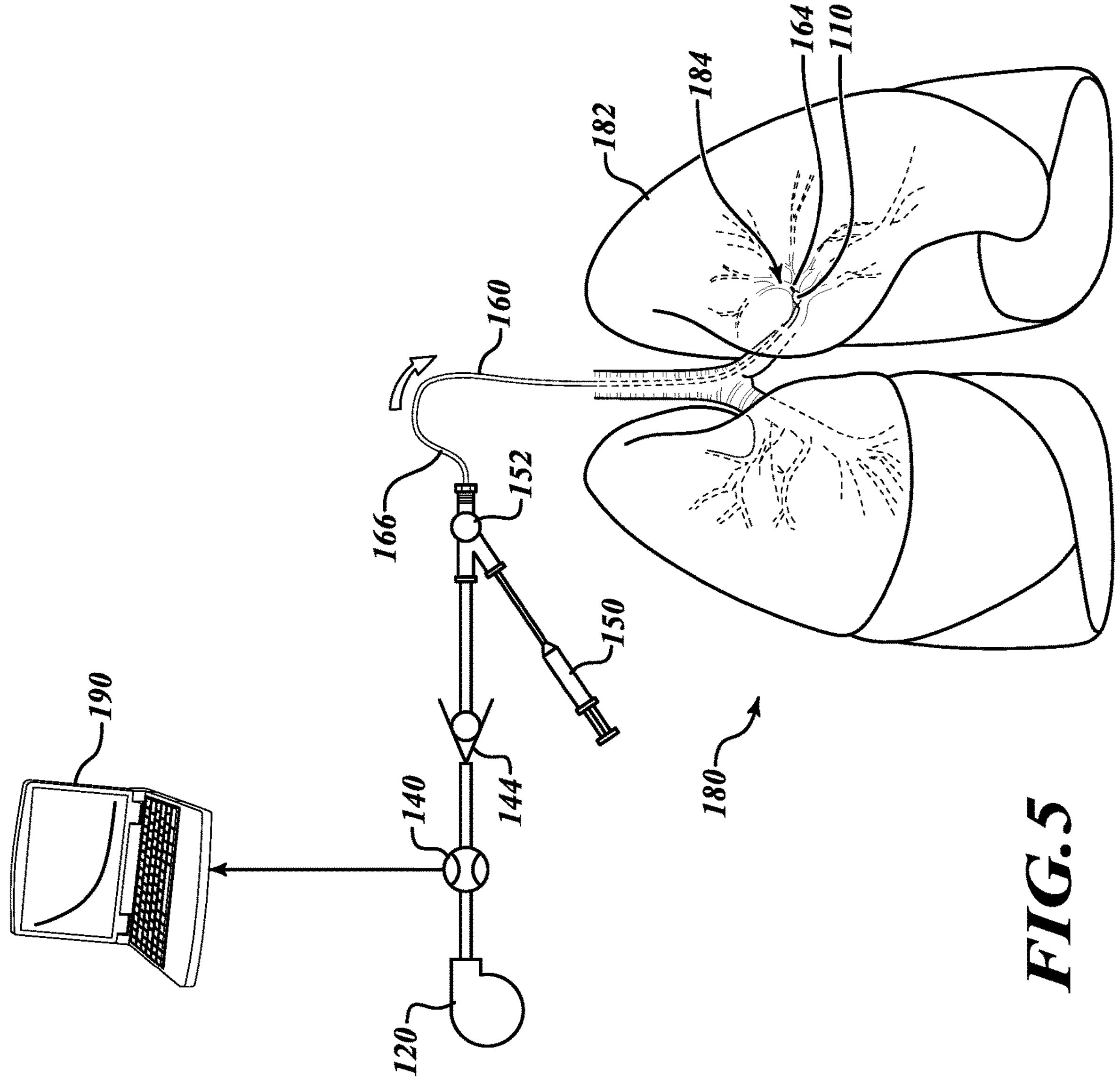
FIG. 5 is a schematic diagram of an illustrative system for assessing collateral ventilation.

Referring additionally to FIG. 5, in various embodiments the sensor system 20 may include a pressure source 120 that is couplable to the flow lumen 160 to provide the positive pressure flow to the lobe 182. A check valve 144 is positionable between the pressure source 120 and the flow lumen 160 to permit the positive pressure flow to the lobe 182 and prevent a backflow of pressure from the lobe 182 through the flow lumen 160. A flow meter 140 is couplable to the flow lumen 160 to measure the positive pressure flow to the lobe 182. A measurement apparatus 190 is couplable with the flow meter 140 to monitor changes in the positive pressure flow to the lobe 182 over time to assess a presence of collateral ventilation out of the lobe 182. Operation of the system 110 and assessing collateral ventilation is performed by the measurement apparatus 190, the operation of which is further described below with reference to FIGS. 6-18.

Referring back to FIG. 5, once the occlusion device 110 is in place and the lobe 184 is thus occluded, other components of the system 100 are used to assess potential collateral ventilation out of the lobe 184. The pressure source 120 is activated to commence a flow of positive pressure via the flow lumen 160, thereby introducing a positive pressure flow into the occluded lobe 184 downstream of the occluded bronchial passageway 184. In various embodiments, the pressure source 120 may be an air pump, such as a continuous positive airway pressure (CPAP) device as commonly used by sleep apnea patients. The pressure source 120 is configured to generate a pressure that is tolerable and noninjurious even to potentially weakened or damaged lungs. In various embodiments, the positive pressure may be set to 15 centimeters of water (cm $H_2O$) or in a range of 10 to 15 cm $H_2O$ with a volumetric flow up to 500 milliliters (mL) per minute. This pressure typically may be substantially lower than that generated by ventilators and respirators used for inpatient hospital care. The pressure source 120 may include a pump motor that drives an impeller or other mechanism in a pump (not shown in FIG. 1). The pump maintains a steady pressure in a reservoir (not shown in FIG. 1). A pressure gauge monitors the pressure in the reservoir and, via a feedback path, controls operation of the pump motor to maintain a constant pressure in the reservoir (not shown in FIG. 1).

An output of the pressure source 120 passes through the flow meter 140. In various embodiments, the flow meter 140 includes an electronic mass flow meter. Using an electronic mass flow meter enables electronic monitoring of the pressure flow by the measurement apparatus 190. Also, using an electronic mass flow meter, rather than a mechanical flow meter, provides a more accurate reading of the flow to be able to discern even small changes in flow of gas through the flow lumen 160 into the occluded lobe 182 that may indicate the presence of collateral ventilation out of the occluded lobe 184.

Downstream of the flow meter, the check valve 144 blocks a flow of pressure back from the flow lumen 160. However, to allow the flow generated by the pressure source 120 at a noninjurious level to be conveyed to the lobe 184, in various embodiments, the check valve 144 should have a low opening or cracking pressure. Specifically, the opening or cracking pressure should be less than one-tenth pound per square inch or on the order of hundredths of pounds per square inch. For example, a Qosina™ "High Flow Check Valve" Model 91008 has a cracking pressure of 0.040 pounds per square inch that is well-suited for use in the system 100. The low cracking pressure of the check valve 144 allows the pressure source 120 to be in the nature of a CPAP device. It will be appreciated that such a device can drive a flow of air into the flow lumen 160 at a level which is noninjurious even to a potentially weakened lobe 184 while still providing a seal against backflow from the flow lumen 160.

Figure 12:
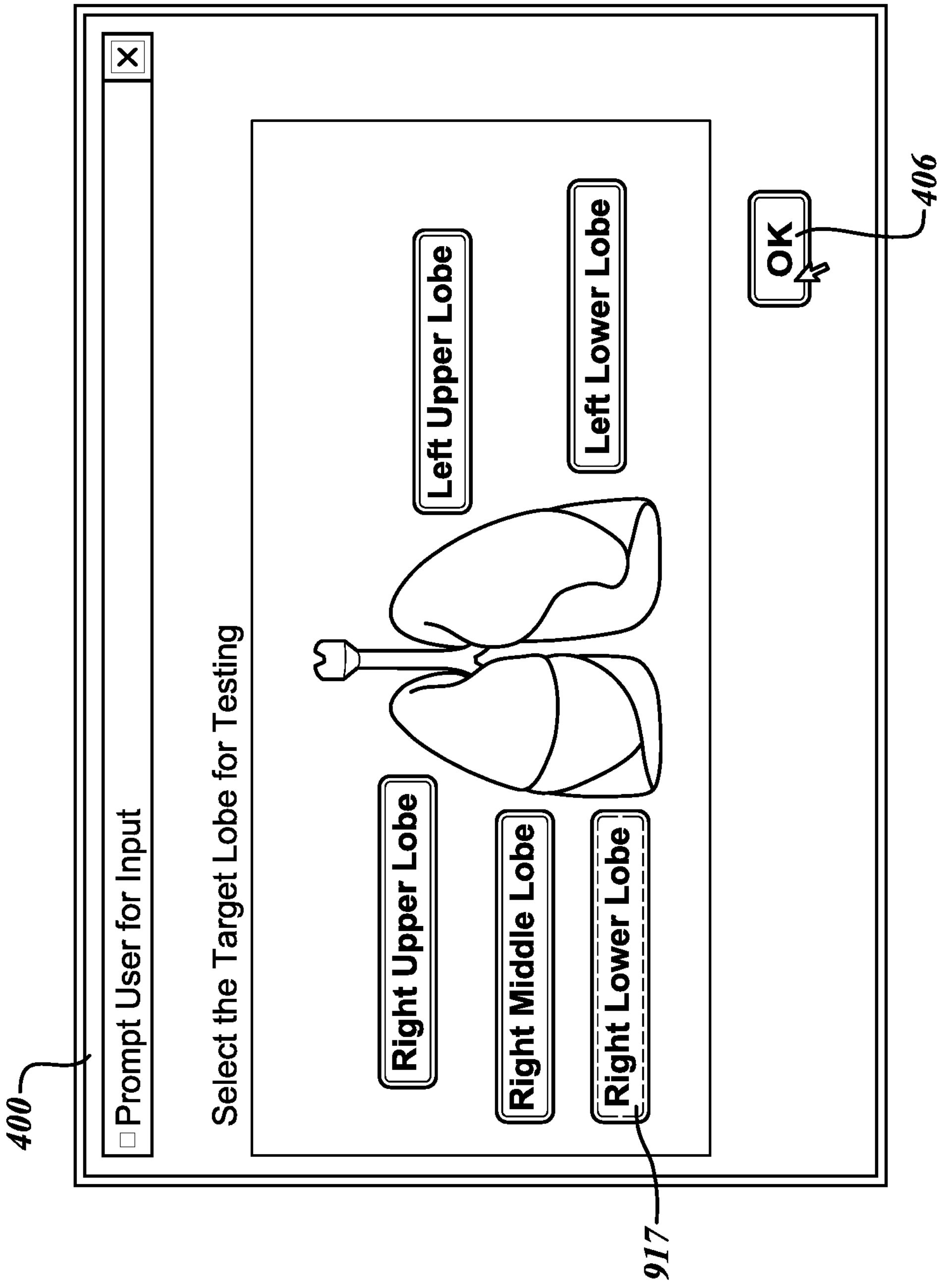
Figure 13:
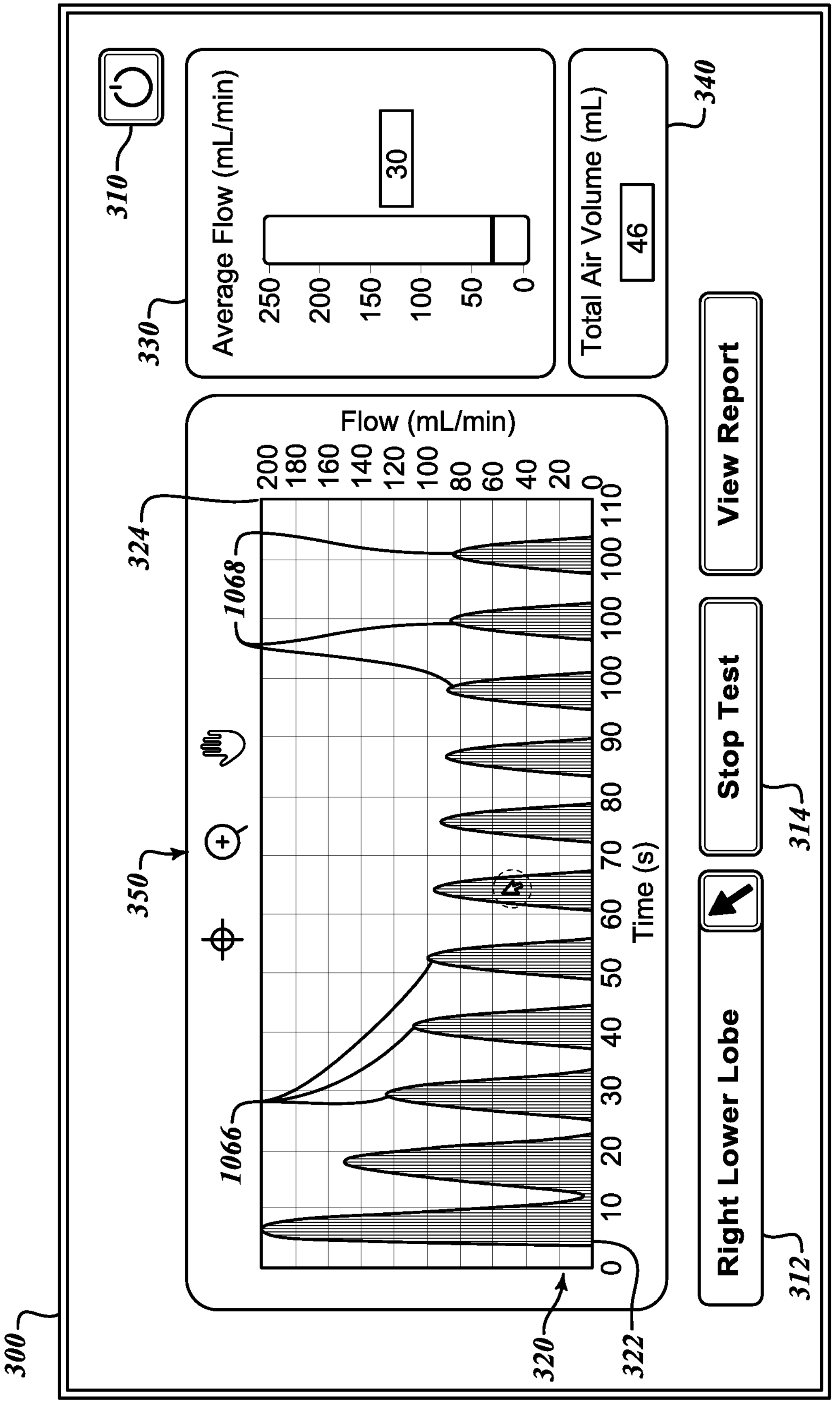
Figure 14:
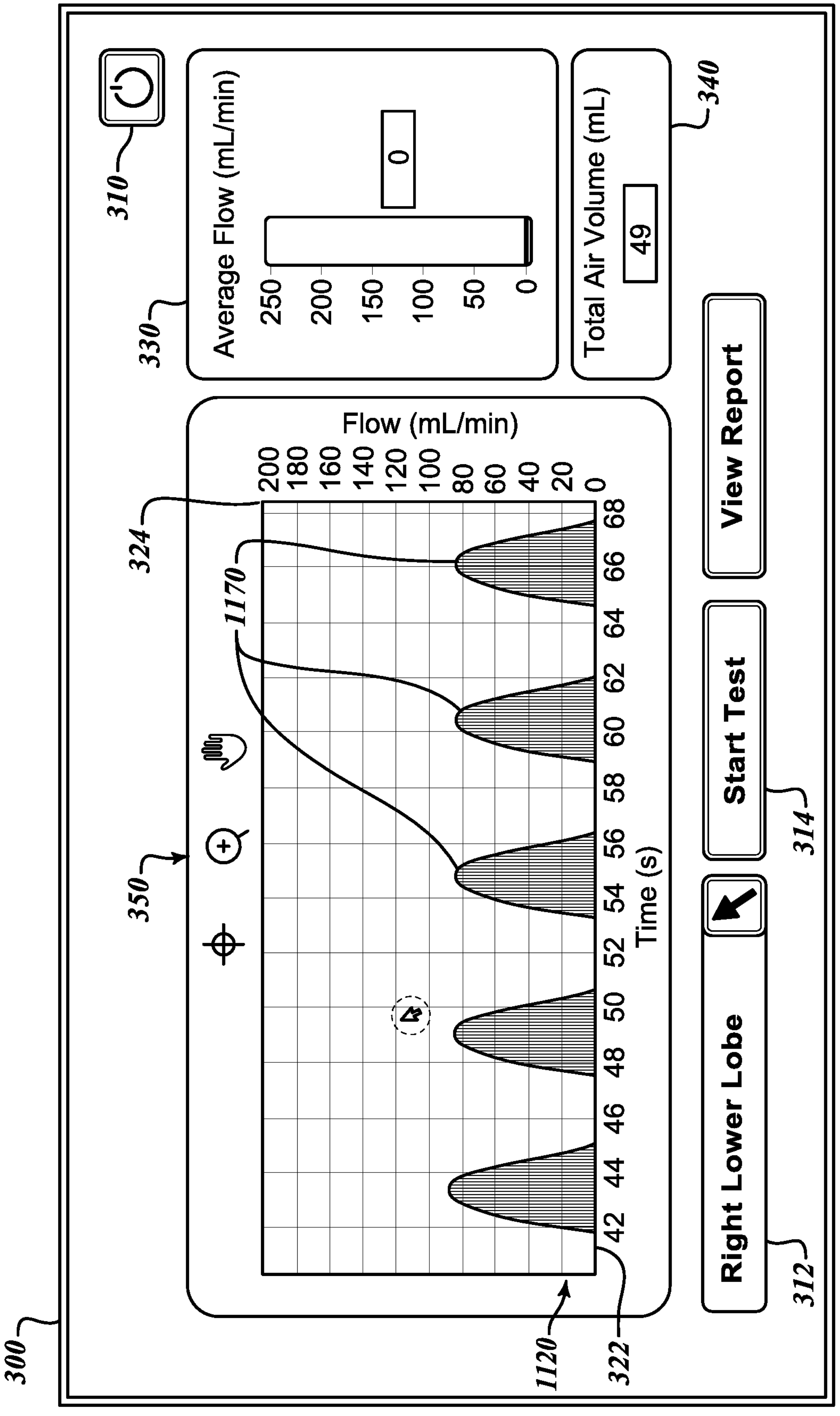

With the lobe 184 occluded by the occlusion device 110 and a pressure prepared to be applied through the flow lumen 160, testing can begin by activating the pressure source 120 and measuring the flow through the flow lumen 160 into the occluded lobe 184 using the flow meter 140. The measured flow may be monitored with the measurement apparatus 190, as described with reference to FIGS. 6-14. FIGS. 6-11 illustrate an example in which the system 100 determines that there is no collateral ventilation from the occluded lobe 184. FIGS. 12-14 illustrate an example in which the system 100 detects that there is collateral ventilation from the occluded lobe 184.

Figure 6:
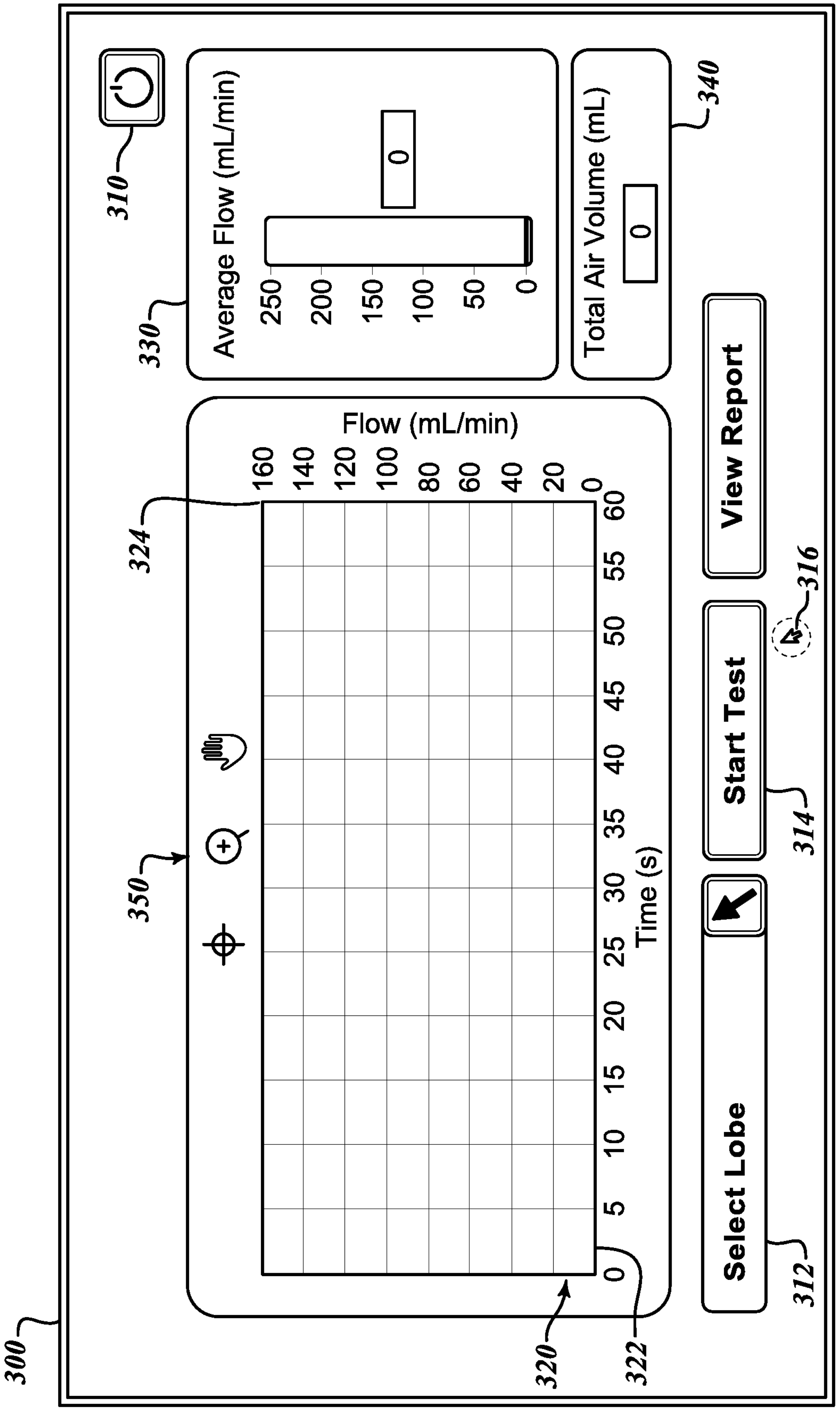
FIGS. 6 through 14 are display screens from an interface in a system for assessing collateral ventilation.

Referring to FIG. 6, at an interface screen 300 in an initial state, a user is provided with a choice of various command options. In various embodiments, the measurement apparatus 190 includes a computing system with a graphical user interface controlled by a mouse, a keyboard, or other input devices. In other embodiments, the measurement apparatus 190 includes a touch-screen. In any case, the interface screen 300 provides user inputs including a power option 310 to turn off the system, a select lobe button 312 to identify the lobe being tested, and a start button 314 to initiate the test. The interface screen 300 also includes a flow display 320 that includes an independent axis 322 to track a time of the test against which is plotted a measured flow plotted on a dependent axis 324. The interface screen 300 also includes an average flow indicator 330 and a total air volume indicator 340. As described below, once the test is commenced, the flow display 320, the average flow indicator 330, and the total air volume indicator 340 present data for these various measurements. The interface screen 300 also includes display controls 350 to enable the user to focus on or magnify portions of the flow display 320 to more closely study the measurements being reported.

Still referring to FIG. 6, a user may engage the select lobe button 312 to identify the lobe where the occlusion device is positioned to isolate the lobe to test it for collateral ventilation. The user may engage the select lobe button 312 by manipulating a cursor 316 that controlled by an input device or, in the case of a touch screen, by touching the select lobe button 312.

Figure 7:
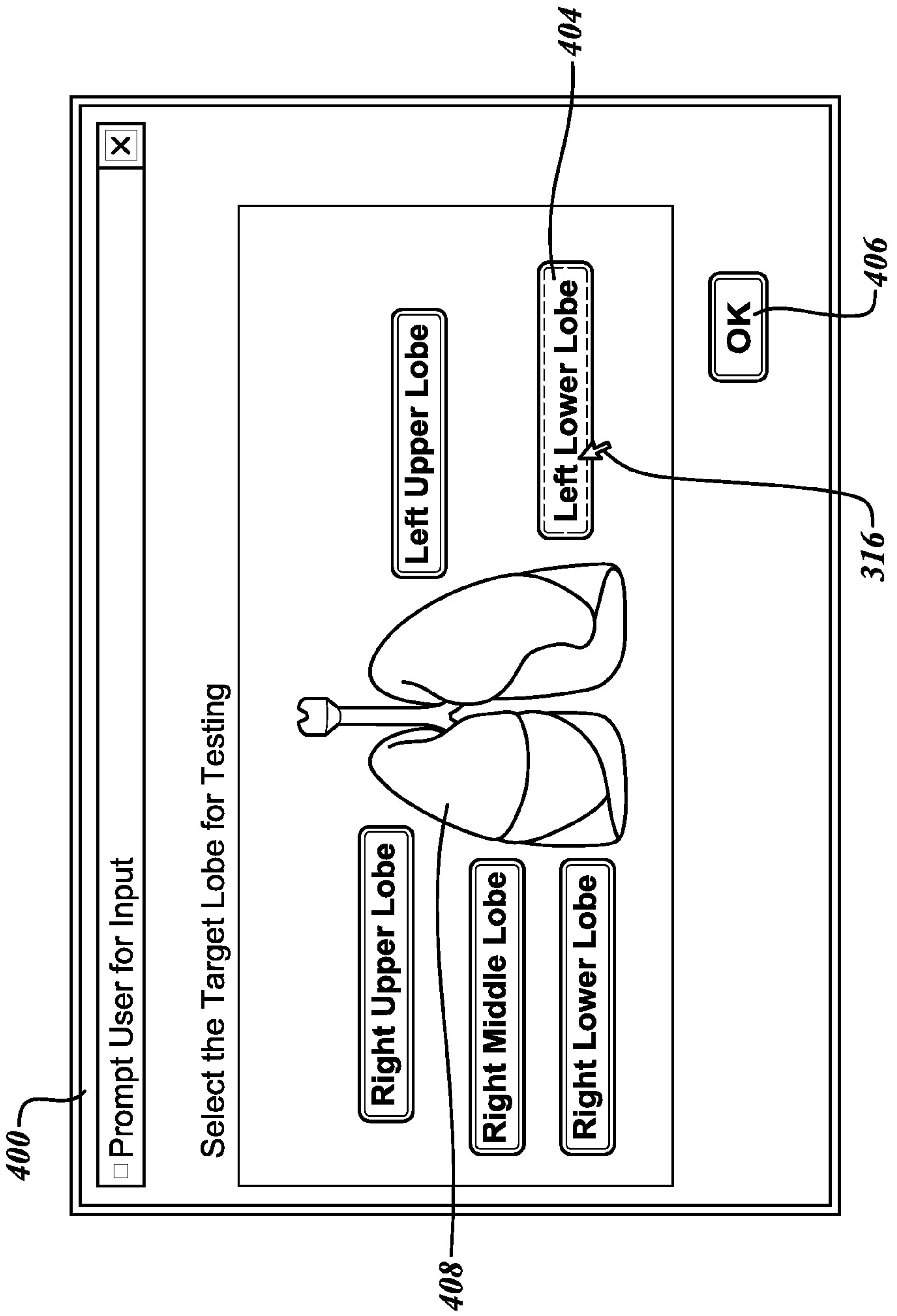

Referring to FIG. 7, upon activating the select lobe button 312 (FIG. 6), the user is presented with a select lobe screen 400. From the select lobe screen 400, the user may identify the lobe being tested by manipulating the cursor 316 to a lobe button 404 that corresponds with the lobe being tested and then selecting an enter or OK button 406 to confirm the selection. Alternatively, the user may identify the lobe being tested by manipulating the cursor 316 to select the lobe to be tested from a lobe map 408.

Figure 8:
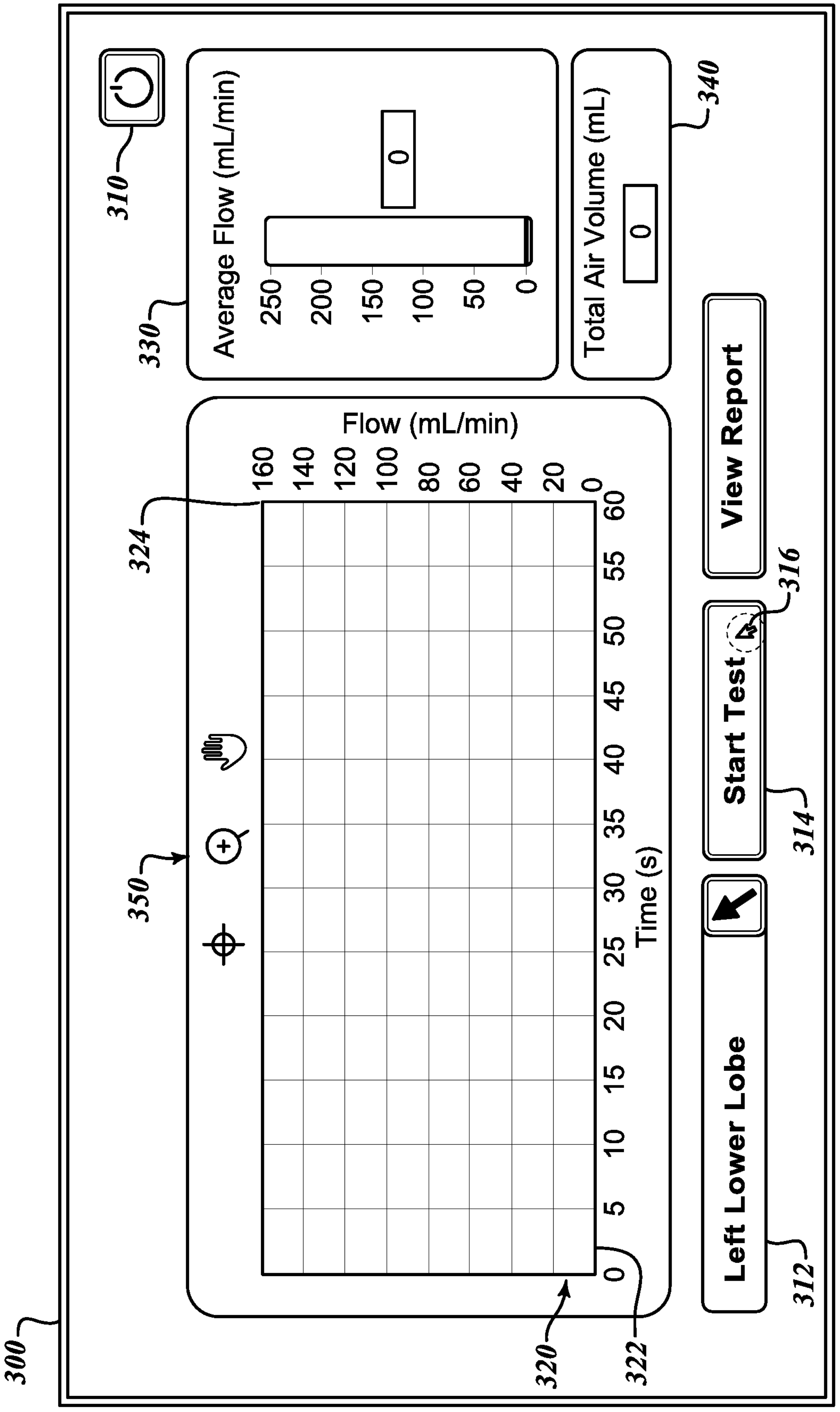

Referring to FIG. 8, after identifying that the "Left Lower Lobe" is to be tested (FIG. 7), the user is returned to the interface screen 300 to initiate the test. To initiate the test, the user may direct the cursor 316 to select the start button 314. Because the test has not yet commenced, it will be appreciated that none of the flow display 320, the average flow indicator 330, or the total air volume indicator 340 shows any flow readings.

Figure 9:
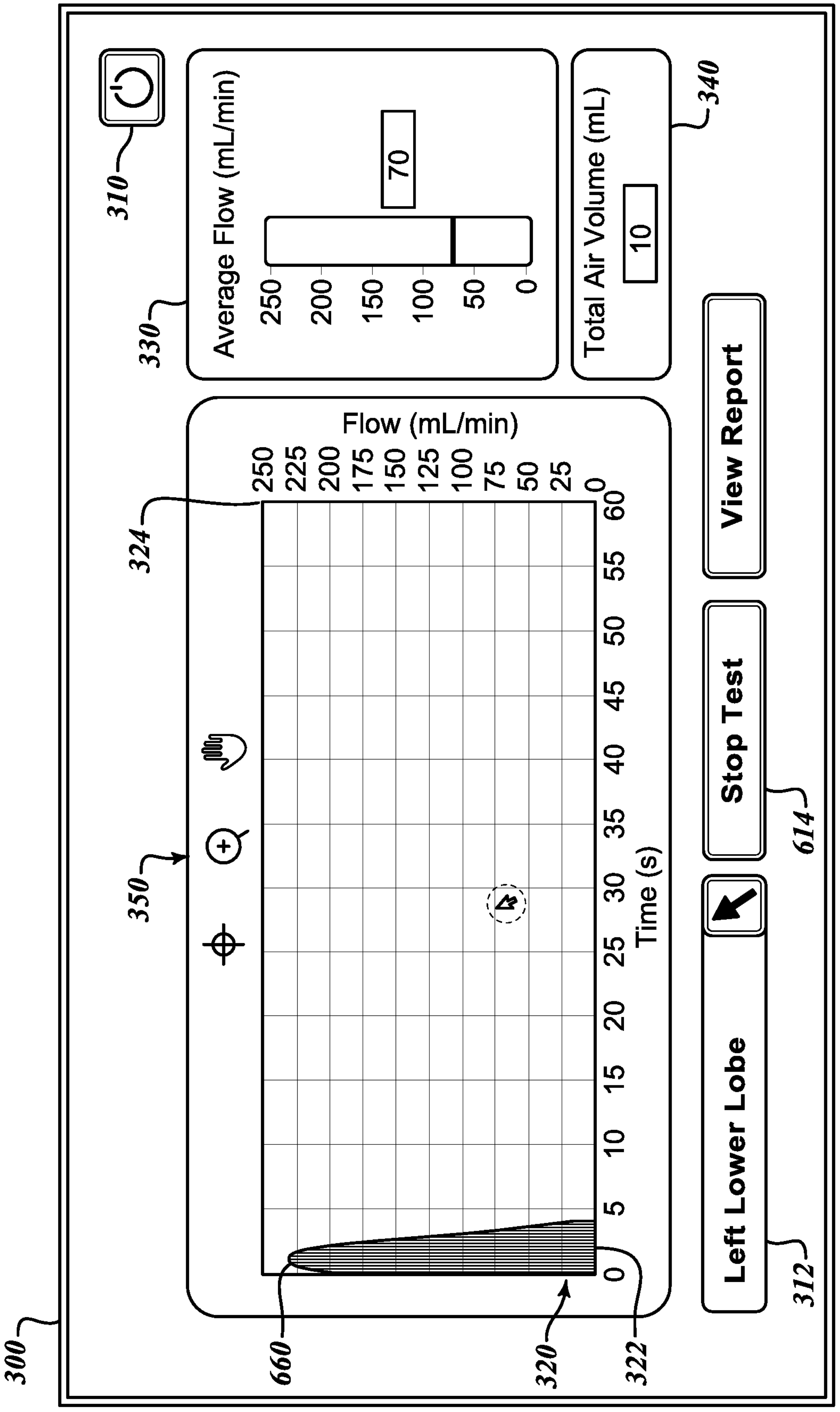

Referring to FIG. 9, the test has commenced. The flow display 320 displays a first curve 660 that shows an initial flow measurement corresponding with a patient's breath. In various embodiments, a scale of the dependent axis 324 that shows the flow is adjusted to fit the first curve. It will be appreciated that, with the commencement of the test and the flow from the pressure source 120 (FIG. 5), the flow may be expected to be at its highest level as the occluded lobe begins to be filled from the flow lumen 160 (FIG. 5) with the least amount of pressure to oppose the flow in the isolated lobe beyond the occlusion device (FIG. 5). The average flow indicator 330 and the total air volume indicators 340 present new values to reflect the measured flow resulting from the commencement of the test. With the commencement of the test, the start button 314 (FIG. 8) has toggled to present a stop button 614 to end the test.

Figure 10:
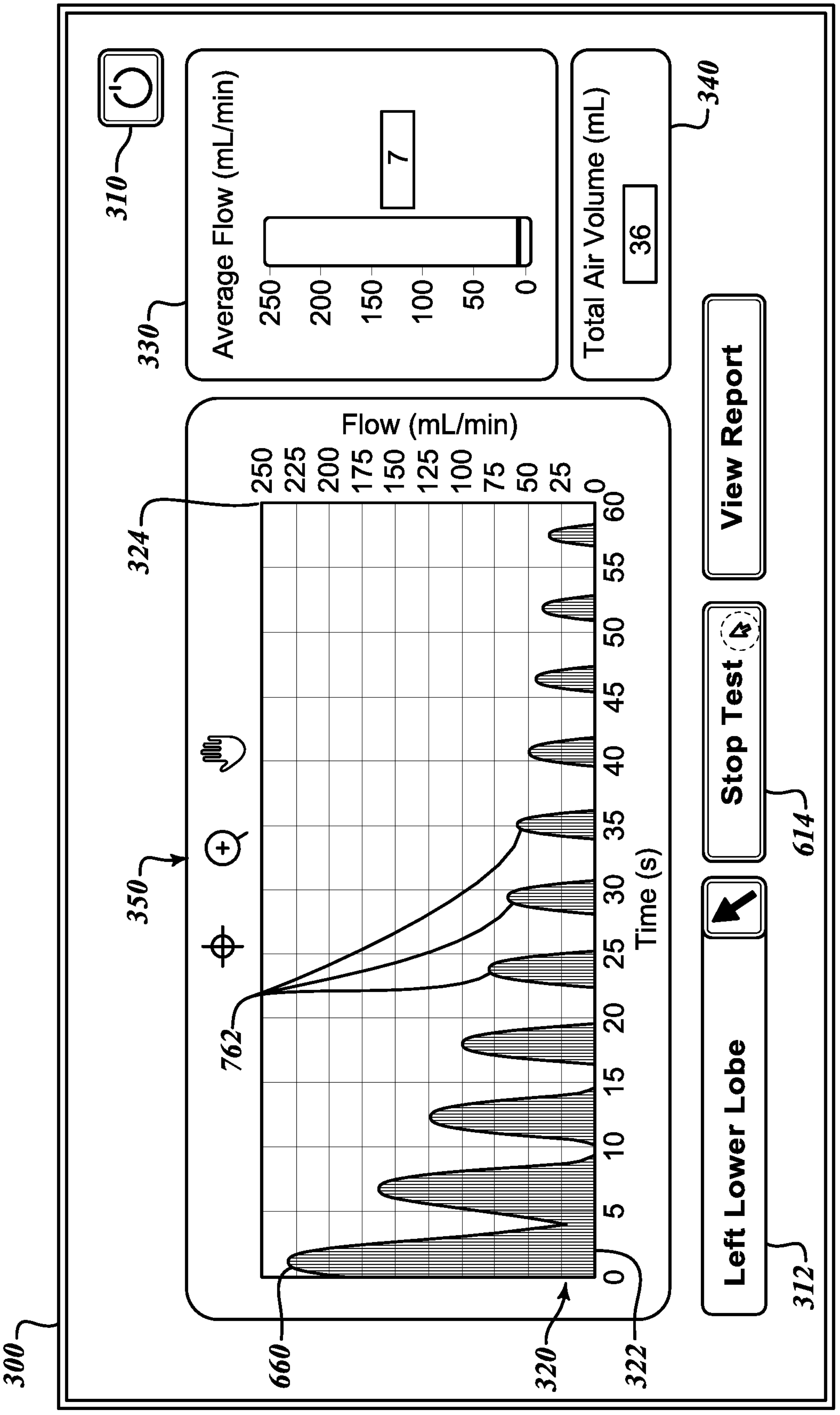

Referring to FIG. 10, after approximately one minute of testing, the flow display 320 presents a first set of additional curves 762 that plot flow versus time. From the first curve 660 through the first set of additional curves 762, it can be seen that the measured flow over time steadily decreases. Although the total air volume indicator 340 understandably reports a rising total volume because the flow has continued over the course of the test, the average flow indicator 330 indicates that the average flow is decreasing, thereby indicating that the occluded lobe is resisting further flow of air from the pressure source 160 (FIG. 5).

Figure 11:
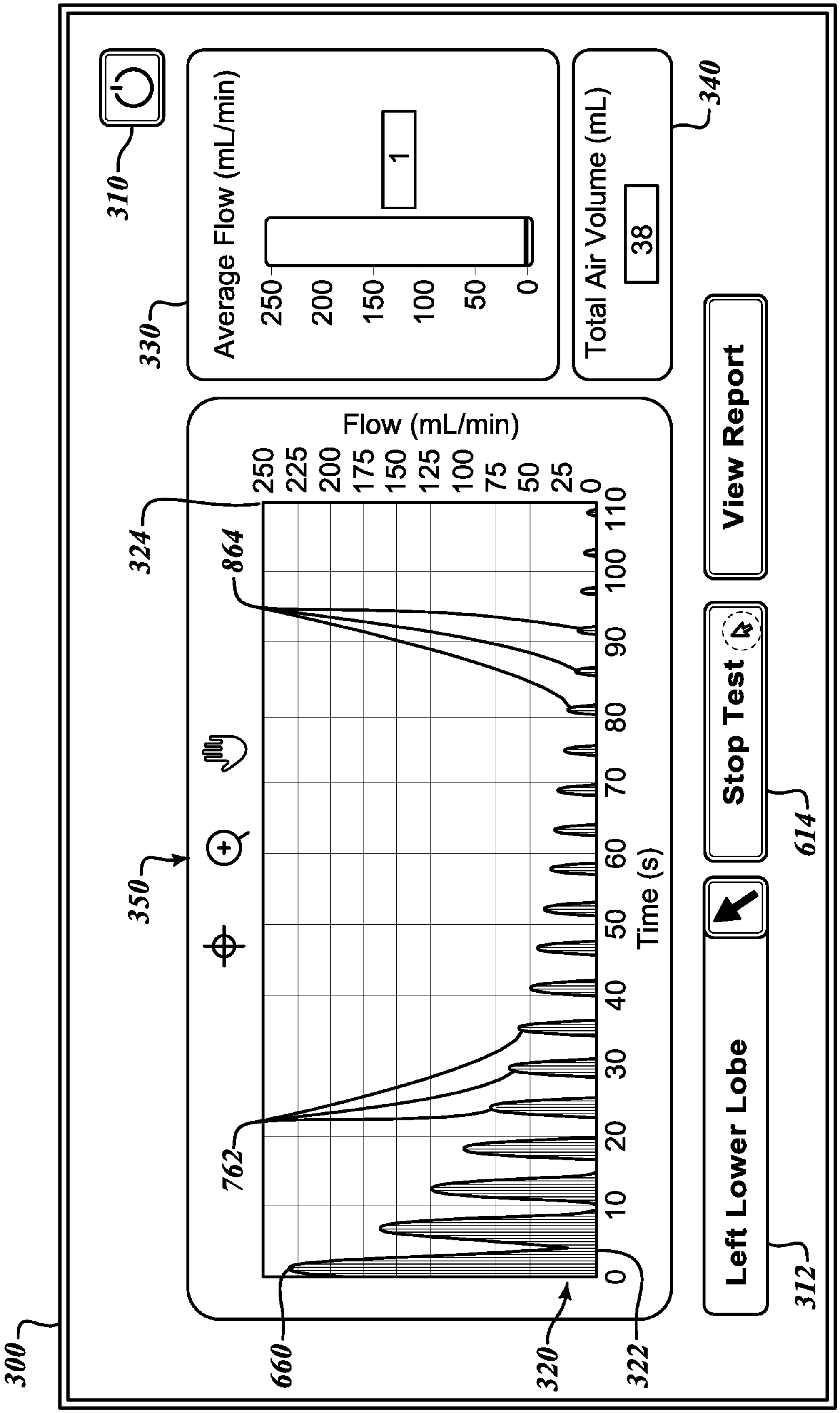

Referring to FIG. 11, after nearly another minute of testing, the flow display 320 presents a second set of additional curves 864 that shows a further diminution of flow over time. The trend shows that occluded lobe is resisting the continuing flow of air, thereby indicating that pressure is not leaking from the occluded lobe. While the total air volume indicator 340 is further incremented to report the total volume over the course of the test, the average flow indicator 330 indicates that the average flow has further decreased, thereby confirming that the occluded lobe is further resisting any additional flow of air from the pressure source 160 (FIG. 5). Therefore, it can be determined that there is no collateral ventilation from the occluded lobe being tested. At the conclusion of the test, the user may engage the stop test button 614 to end the test.

Referring to FIG. 12, to test another lobe a user proceeds again to the select lobe screen 400 (having again selected the select lobe button 312 as described with reference to FIG. 8). From the select lobe screen 400, the user identifies the lobe to be tested by selecting a corresponding lobe button 917 and then selecting the enter or OK button 406 to confirm the selection.

Referring to FIG. 13, after little more than one minute of testing, the flow display 320 presents additional curves 1066 and 1068 that plot flow versus time. In the first set of curves 1066, the measured flow over time steadily decreases. However, in the second set of curves 1068, the measured flow over time no longer decreases. The average flow indicator 330 also stabilizes to indicate a continuing stable flow. The steady flow indicates a positive collateral ventilation out of the lobe being tested. Referring to FIG. 14, to more closely study selected curves 1170 on the flow display, a user may engage the display controls 350 to show an enlarged portion of the flow display 1120 to verify that the flow is non-decreasing.

Figure 15:
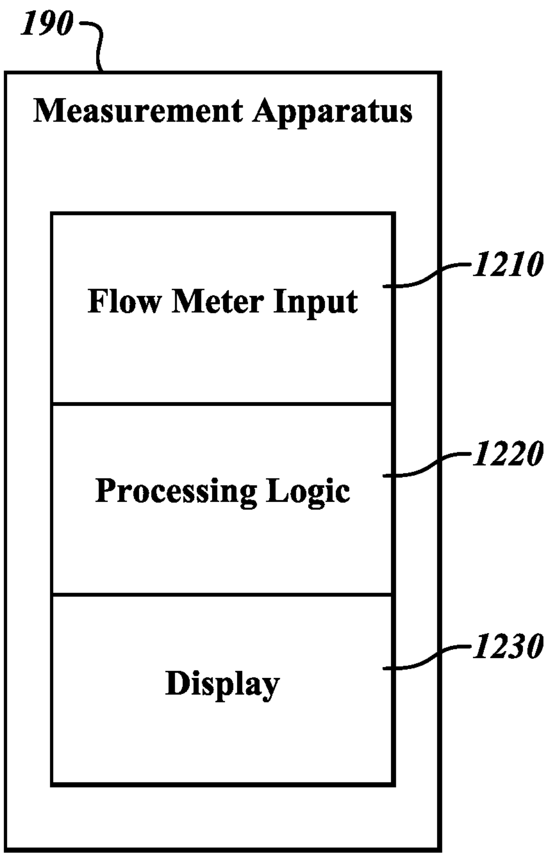
FIG. 15 is a block diagram of an illustrative apparatus for monitoring positive pressure flow into an occluded lobe of a lung.

Referring to FIG. 15, an illustrative embodiment of the measurement apparatus 190 is couplable with the flow meter 140 (not shown in FIG. 15) to monitor positive pressure flow through the flow lumen 160 (not shown in FIG. 15) to determine whether collateral ventilation is occurring from the occluded lobe 182 (not shown in FIG. 15). The measurement apparatus 190 includes a flow meter input 1210, processing logic 1220, and a display 1230. The flow meter input 1210 receives an output of the flow meter 140. As previously described with reference to FIG. 5, in various embodiments, the flow meter 140 includes an electronic mass flow meter with an electronic output to enable electronic monitoring of the pressure flow by the measurement apparatus 190. The flow meter input 1210 may include analog or digital signal lines configured to receive the output of the flow meter 140. The flow meter input 1210 may include a coupling to receive the output of the flow meter 140 or the flow meter input 121 may be hard-wired to the output of the flow meter 140.

The processing logic 1220 includes an electronic circuit or comparable system that is operably coupled to the flow meter input 1210 to receive data from the flow meter 140 and to the display 1230 to display data to the user indicative of whether collateral ventilation exists in the lobe being tested. The processing logic 1220 may include a computing system as further described with reference to FIG. 16. The processing logic 1220 is operably coupled with the flow meter input 1210 and the display 1230. The processing logic 1220 includes circuitry configured to monitor data received from the flow meter 140 via the flow meter input 1210, process the data, and generate a displayable signal to the display 1230. In various embodiments, the display 1230 includes a device that receives an electronic signal and converts that signal into a graphical representation viewable by a user. Using the display 1230, a user can monitor whether the flow of positive pressure into the occluded lobe of the lung being tested indicates the presence of collateral ventilation, as described with reference to FIGS. 6-14.

Figure 16:
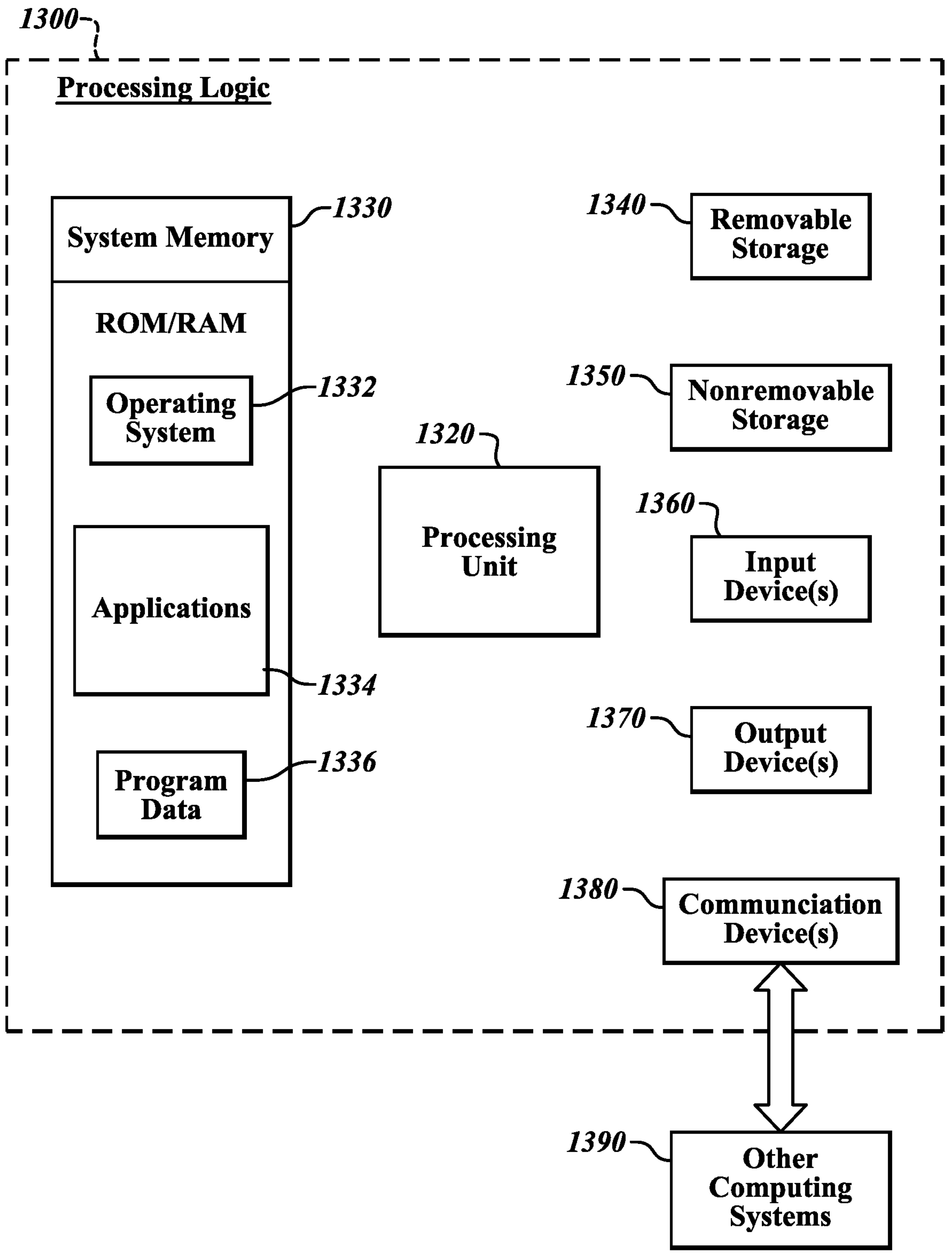
FIG. 16 is a block diagram of an illustrative computing system configurable for use in the apparatus of FIG. 15.

Referring to FIG. 16, the processing logic 1220 (FIG. 14) may include a computing system 1300. The computing system 1300 may include any of a number of forms of stationary or mobile computing devices. The computing system 1300 typically includes at least one processing unit 1320 and a system memory 1330. Depending on the exact configuration and type of computing device, the system memory 1330 may be volatile (such as RAM), non-volatile (such as ROM, flash memory, and the like) or some combination of the two. The system memory 1330 typically maintains an operating system 1332, one or more applications 1334, and program data 1336. The operating system 1332 may include any number of operating systems executable on desktop or portable devices including, but not limited to, Linux, Microsoft Windows, Apple OS, or Android. The one or more applications 1334 include instructions for receiving and processing the flow meter data and generating displayable information, as previously described with reference to FIGS. 6-14.

The computing system 1300 may also have additional features or functionality. For example, the computing system 1300 may also include additional data storage devices (removable and/or non-removable) such as, for example, magnetic disks, optical disks, tape, or flash memory. Such additional storage is illustrated in FIG. 16 by removable storage 1340 and non-removable storage 1350. Computer storage media may include volatile and non-volatile, removable and non-removable media implemented in any method or technology for storage of information, such as computer readable instructions, data structures, program modules or other data. The system memory 1330, the removable storage 1340, and the non-removable storage 1350 are all examples of computer storage media. Available types of computer storage media include, but are not limited to, RAM, ROM, EEPROM, flash memory (in both removable and non-removable forms) or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by the computing system 1330. Any such computer storage media may be part of the computing system 1330.

In various embodiments, the computing system 1330 may also have input device(s) 1360 such as a keyboard, mouse, pen, voice input device, touchscreen input device, etc. Output device(s) 1370 such as a display, speakers, printer, short range transceivers such as a Bluetooth transceiver, etc., may also be included. In various embodiments, the computing system 1330 may include a touch-sensitive display which integrates attributes of an output device 1370 and an input device 1360, enabling a user to interact with information and user-selectable controls presented via the display. Thus, the display 1230 of the measurement apparatus 190 may include a touch-sensitive display enabling a user to control operations of the measurement apparatus 190 and review information presented by the measurement apparatus 190.

The computing system 1300 also may include one or more communication connections 1380 that allow the computing system 1300 to communicate with other computing systems 1390, such as over a wired or wireless network or via Bluetooth (a Bluetooth transceiver may be regarded as an input/output device and a communications connection). The one or more communication connections 1380 are an example of communication media. Available forms of communication media typically carry computer readable instructions, data structures, program modules or other data in a modulated data signal such as a carrier wave or other transport mechanism and includes any information delivery media. The term "modulated data signal" may include a signal that has one or more of its characteristics set or changed in such a manner as to encode information in the signal. By way of example, and not limitation, communication media may include wired media such as a wired network or direct-wired connection, and wireless media such as acoustic, RF, infrared and other wireless media. The term computer readable media as used herein includes both storage media and communication media.

Figure 17:
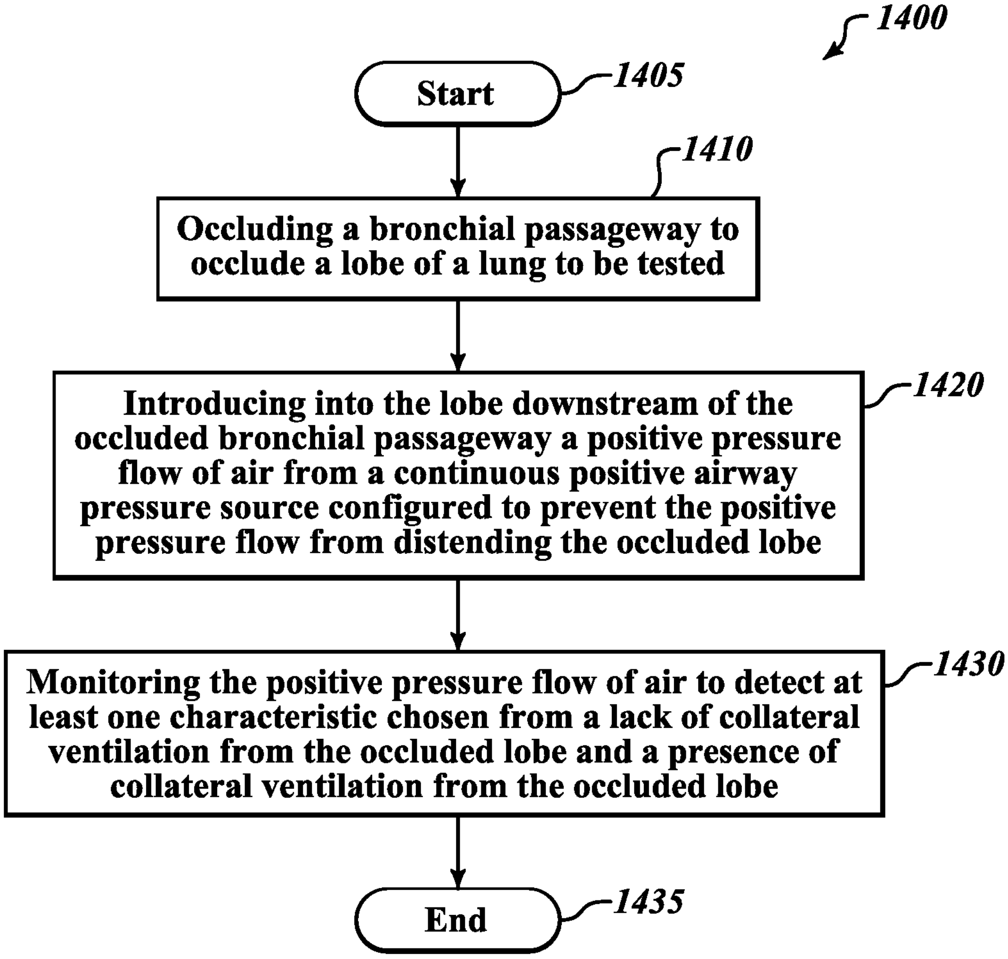
FIG. 17 is a flow diagram of an illustrative method of evaluating measurements from a flow meter positioned to assess potential ventilation from an occluded lobe of a lung.

Referring to FIG. 17, in various embodiments an illustrative method 1400 of testing for collateral ventilation is provided. The method 1400 starts at a block 1405. At a block 1410, a bronchial passageway is occluded to occlude a lobe of a lung as previously described with reference to FIGS. 1-4. At a block 1420, a positive pressure flow of air from a continuous positive airway pressure source configured to prevent the positive pressure flow from distending the occluded lobe is introduced into the occluded lobe downstream of the occluded bronchial passageway, as also previously described with reference to FIGS. 1A and 1B. At a block 1430, the positive pressure flow of air is monitored to detect at least one characteristic chosen from a lack of collateral ventilation from the occluded lobe and a presence of collateral ventilation from the isolated lobe, as previously described with reference to FIGS. 6-14. The method 1400 ends at a block 1435.

Figure 18:
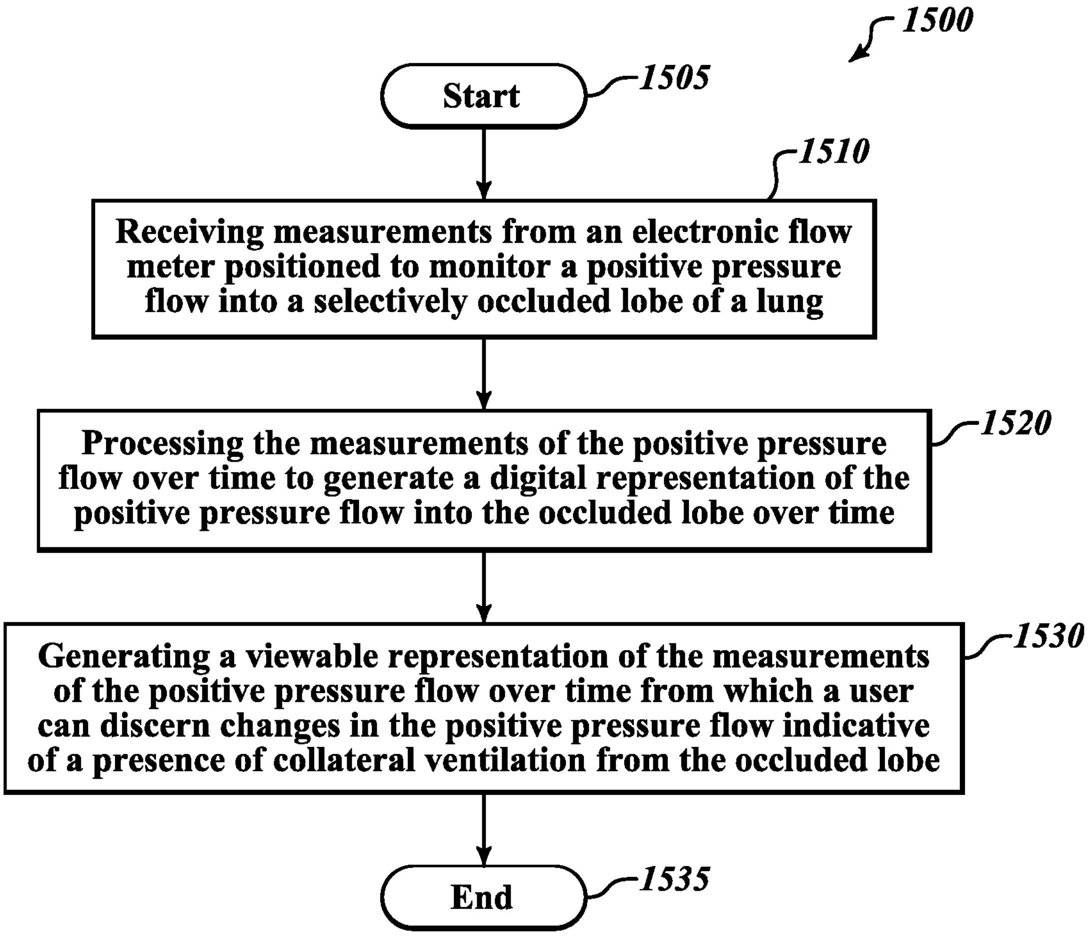
FIG. 18 is a flow diagram of an illustrative method of generating a viewable representation of measurements of a positive pressure flow into an occluded lobe of a lung.

Referring to FIG. 18, in various embodiments an illustrative method 1500 is provided for generating a viewable representation of positive pressure flow into a lobe of a lung to assess possible collateral ventilation. The method 1200 starts at a block 1505. At a block 1510, measurements are received from an electronic flow meter positioned to monitor a positive pressure flow into a selectively occluded lobe of a lung, as previously described with reference to FIGS. 1A and 1B. At a block 1520, the measurements of the positive pressure flow over time are processed to generate a digital representation of the positive pressure flow over time, as previously described with reference to FIGS. 6-16. At a block 1530, a viewable representation of the measurements of the positive pressure flow over time is generated from which a user can discern changes in the positive pressure flow indicative of a presence of collateral ventilation from the lobe, as also previously described with reference to FIGS. 6-16. As previously described, detecting a measurable flow that continues to decrease over time indicates a lack of collateral ventilation from the lobe, while detecting a measurable flow that stabilizes over time may indicate a presence of collateral ventilation. The method 1500 ends at a block 1535.

EMBODIMENTS

A. A flexible insertion catheter device comprising: an outer tube having an inner diameter, the outer tube including: a plurality of ports at a distal end; and an occlusion device filling port located proximal from the plurality of ports; an inner tube receivable within the outer tube, the inner tube includes a flow lumen and an outer diameter less than the inner diameter of the outer tube; and an occlusion device attachable to the outer tube and configured to selectively seal a bronchial passageway to occlude a lobe of a lung.

B. The device of A, wherein the outer tube includes: a rounded distal end.

C. The device of B, wherein the plurality of ports are located through a side of the outer tube.

D. The device of any of A-C, further comprising: a seal located between the flow lumen and an inflation lumen located between the outer tube and the inner tube.

E. The device of D, wherein the inflation lumen is configured to receive from an inflation device a flow of gas to selectively inflate and expand the occlusion device to sealably occlude the bronchial passageway.

F. The device of D or E, wherein the inner tube extends distal from the seal.

G. The device of F, wherein the inner tube includes a plurality of ports distal of the seal.

H. The device of G, wherein: one or more of the plurality of ports of the inner tube has a first diameter value; one or more of the plurality of ports of the outer tube has a second diameter value; and the first diameter value is greater than the second diameter value.

I. The device of G or H, wherein the plurality of ports of the inner tube are offset at least one of radially or longitudinally from the plurality of ports of the outer tube.

J. An apparatus comprising: a flexible insertion catheter comprising: an outer tube having an inner diameter, the outer tube including: a plurality of ports at a distal end; and an occlusion device filling port located proximal from the plurality of ports; an inner tube receivable within the outer tube, the inner tube includes a flow lumen and an outer diameter less than the inner diameter of the outer tube; and an occlusion device attachable to the outer tube and configured to selectively seal a bronchial passageway to occlude a lobe of a lung; an inflation device configured to selectively inflate the occlusion device; and an air supply device configured to supply air through the inner tube.

K. The apparatus of J, wherein the outer tube includes: a rounded distal end; and a side surface having a normal vector being perpendicular to a longitudinal axis of the outer tube.

L. The apparatus of K, wherein the plurality of ports are located through the side surface.

M. The apparatus of any of J-L, wherein the flexible insertion catheter includes a seal located between the flow lumen and an inflation lumen located between the outer tube and the inner tube.

N. The apparatus of M, wherein the inflation lumen is configured to receive from the inflation device a flow of gas to selectively inflate and expand the occlusion device to sealably occlude the bronchial passageway.

O. The apparatus of M or N, wherein the inner tube extends distal from the seal.

P. The apparatus of O, wherein the inner tube includes a plurality of ports distal of the seal.

Q. The apparatus of P, wherein: one or more of the plurality of ports of the inner tube has a first diameter value; one or more of the plurality of ports of the outer tube has a second diameter value; and the first diameter value is greater than the second diameter value.

R. The apparatus of P or Q, wherein the plurality of ports of the inner tube are offset at least one of radially or longitudinally from the plurality of ports of the outer tube.

S. A method comprising: providing an outer tube having an inner diameter, a plurality of ports at the distal end, and an occlusion device filling port proximal from the plurality of ports; providing an inner tube receivable within the outer tube, the inner tube includes a flow lumen and an outer diameter less being than the inner diameter of the outer tube; and providing an occlusion device attachable to the outer tube and configured to selectively seal a bronchial passageway to occlude a lobe of the lung.

T. The method of S, further comprising: providing a plurality of ports to the inner tube distal of the seal, wherein: one or more of the plurality of ports of the inner tube has a first diameter value; one or more of the plurality of ports of the outer tube has a second diameter value; the first diameter value is greater than the second diameter value; and the plurality of ports of the inner tube are offset at least one of radially or longitudinally from the plurality of ports of the outer tube.

It will be appreciated that the detailed description set forth above is merely illustrative in nature and variations that do not depart from the gist and/or spirit of the claimed subject matter are intended to be within the scope of the claims. Such variations are not to be regarded as a departure from the spirit and scope of the claimed subject matter.

What is claimed is:

1. A flexible insertion catheter device comprising:

an outer tube having an inner diameter, the outer tube including:

a plurality of ports at a distal end; and an occlusion device filling port located proximal from the plurality of ports through a sidewall of the outer tube;

an inner tube receivable within the outer tube, the inner tube includes a flow lumen and an outer diameter less than the inner diameter of the outer tube, a distal end of the inner tube terminates proximal of the plurality of ports in the outer tube, wherein the flow lumen is configured to provide fluid communication between a proximal end of the flexible insertion catheter and the plurality of ports;

an annular seal located between an outer surface of the inner tube and an inner surface of the outer tube, the annular seal extending circumferentially around the outer surface of the inner tube to provide a pneumatic seal at a distal end of an inflation lumen located between the outer tube and the inner tube; and an occlusion device affixed to a portion of the outer tube that is proximal at least a portion of the inner tube that is receivable within the outer tube and configured to selectively seal a bronchial passageway to occlude a lobe of a lung.

2. The device of claim 1, wherein the outer tube includes a rounded distal end.

3. The device of claim 2, wherein the plurality of ports are located through a side of the outer tube.

4. The device of claim 1, wherein the inflation lumen is configured to receive from an inflation device a flow of gas to selectively inflate and expand the occlusion device to sealably occlude the bronchial passageway.

5. The device of claim 1, further comprising a distal inner tube extending from within the inner tube distal from the seal.

6. The device of claim 5, wherein the distal inner tube includes a plurality of ports distal of the seal.

7. The device of claim 6, wherein:

one or more of the plurality of ports of the distal inner tube has a first diameter value;

one or more of the plurality of ports of the outer tube has a second diameter value; and the first diameter value is greater than the second diameter value.

8. The device of claim 6, wherein the plurality of ports of the distal inner tube are offset at least one of radially or longitudinally from the plurality of ports of the outer tube.

9. A system comprising:

a flexible insertion catheter comprising:

an outer tube having an inner diameter, the outer tube including:

a plurality of ports at a distal end; and an occlusion device filling port located proximal from the plurality of ports through a sidewall of the outer tube;

an inner tube receivable within the outer tube, the inner tube includes a flow lumen configured to provide fluid communication between a proximal end of the flexible insertion catheter and the plurality of ports and an outer diameter less than the inner diameter of the outer tube, wherein a distal end of the inner tube terminates proximal of the plurality of ports in the outer tube;

an annular seal extending circumferentially around an outer surface of the inner tube to provide a pneumatic seal at a distal end of an inflation lumen located between the outer tube and the inner tube; and an occlusion device attachable to the outer tube and configured to selectively seal a bronchial passageway;

an inflation device configured to selectively inflate the occlusion device; and an air supply device configured to supply air through the inner tube.

10. The system of claim 9, wherein the outer tube includes a rounded distal end.

11. The system of claim 10, wherein the plurality of ports are located through a side of the outer tube.

12. The system of claim 9, wherein the annular seal located between an outer surface of the inner tube and an inner surface of the outer tube is positioned proximal a distal end of the inner tube and distal the occlusion device filling port to direct fluid with the inflation lumen to exit the occlusion device filling port located between the outer tube and the inner tube.

13. The system of claim 12, wherein the inflation lumen is configured to receive from the inflation device a flow of gas to selectively inflate and expand the occlusion device to sealably occlude the bronchial passageway.

14. The system of claim 12, further comprising a distal inner tube extending from within the inner tube distal from the seal.

15. The system of claim 14, wherein the distal inner tube includes a plurality of ports distal of the seal.

16. The system of claim 15, wherein:

one or more of the plurality of ports of the distal inner tube has a first diameter value;

one or more of the plurality of ports of the outer tube has a second diameter value; and the first diameter value is greater than the second diameter value.

17. The system of claim 15, wherein the plurality of ports of the distal inner tube are offset at least one of radially or longitudinally from the plurality of ports of the outer tube.

18. A method comprising:

providing an outer tube having an inner diameter, a plurality of ports at a distal end, and an occlusion device filling port proximal from the plurality of ports through a sidewall of the outer tube;

providing an inner tube receivable within the outer tube, the inner tube includes a flow lumen configured to provide fluid communication between a proximal end of the flow lumen and the plurality of ports and an outer diameter less being than the inner diameter of the outer tube, a distal end of the inner tube terminates proximal of the plurality of ports in the outer tube;

forming an annular seal, adjacent a distal end of the inner tube, between an outer circumferential surface of the inner tube and an inner circumferential surface of the outer tube to seal a distal end of an inflation lumen between the outer tube and the inner tube; and providing an occlusion device attached to the outer tube and configured to selectively seal a bronchial passageway to occlude a lobe of a the-lung, wherein the occlusion device is affixed to a portion of the outer tube that is proximal at least a portion of the inner tube.

19. The method of claim 18, further comprising:

providing a distal inner tube extending distally from the inner tube;

providing a plurality of ports to the distal inner tube distal of the annular seal, wherein:

one or more of the plurality of ports of the distal inner tube has a first diameter value;

one or more of the plurality of ports of the outer tube has a second diameter value;

the first diameter value is greater than the second diameter value; and the plurality of ports of the distal inner tube are offset at least one of radially or longitudinally from the plurality of ports of the outer tube.

* * * * *